US005760064A

United States Patent [19]
Vazquez et al.

[11] Patent Number: 5,760,064
[45] Date of Patent: *Jun. 2, 1998

[54] SULFONYLALKANOYLAMINO HYDROXYETHYLAMINO SULFANAMIDES USEFUL AS RETROVIRAL PROTEASE INHIBITORS

[75] Inventors: Michael L. Vazquez, Gurnee; Richard A. Mueller, Glencoe, both of Ill.; John J. Talley, St. Louis, Mo.; Daniel Getman, Chesterfield, Mo.; Gary A. DeCrescenzo, St. Peters, Mo.; John N. Freskos, Clayton, Mo.

[73] Assignee: G.D. Searle, St. Louis, Mo.

[*] Notice: The term of this patent shall not extend beyond the expiration date of Pat. Nos. 5,521,219, 5,508,294, 5,510,388.

[21] Appl. No.: 867,430

[22] Filed: Jun. 6, 1997

Related U.S. Application Data

[60] Continuation of Ser. No. 587,688, Jan. 17, 1996, Pat. No. 5,639,769, which is a division of Ser. No. 110,913, Aug. 24, 1993, Pat. No. 5,521,219, which is a continuation-in-part of Ser. No. 935,071, Aug. 25, 1992, abandoned.

[51] Int. Cl.[6] .......................... A61K 31/38; A61K 31/44; A61K 31/18
[52] U.S. Cl. .......... 514/357; 514/237.8; 514/445; 514/539; 514/602; 514/603; 514/604; 514/605; 544/160; 546/194; 546/234; 549/65; 560/13; 564/80; 564/84; 564/86; 564/87; 564/89; 564/90; 564/91; 564/93; 564/94; 564/95; 564/98; 564/99
[58] Field of Search .................. 514/237.8, 357, 514/445, 539, 602, 603, 604, 605; 544/160; 546/194, 234; 549/65; 560/13; 564/80, 84, 86, 87, 89, 90, 91, 92, 93, 94, 95, 98, 99

[56] References Cited

U.S. PATENT DOCUMENTS

| H725 | 1/1990 | Gordon | 548/533 |
|---|---|---|---|
| 4,599,198 | 7/1986 | Hoover | 260/998.2 |

FOREIGN PATENT DOCUMENTS

| 7982387 | 4/1988 | Australia . |
| 0 264 795 | 4/1988 | European Pat. Off. . |
| 0 342 541 | 11/1989 | European Pat. Off. . |
| 0 346 847 | 12/1989 | European Pat. Off. . |
| 2 184 730 | 7/1987 | United Kingdom . |
| 2 200 115 | 7/1988 | United Kingdom . |
| 2 209 752 | 5/1989 | United Kingdom . |
| 9208701 | 5/1992 | WIPO . |

OTHER PUBLICATIONS

Roberts et al., "Rational Design of Peptide–based Proteinase Inhibitors, "*Science*, 248, 358 (1990).

Erickson et al., "Design Activity, and 2.8A Crystal Structure of a C$_2$ Symmetric Inhibitor Complexed to HIV–1 Protease, "*Science*, 527, (1990).

S.J. Fittkau, *Prakt. Chem.*, 315, 1037 (1973).

Pauwles et al., "Rapid and automated tetrazolium–based colormetric assay for the detection of anti–HIV compounds, "*J.Virol. Methods*, 20, 309–321 (1988).

*Primary Examiner*—Peter O'Sullivan
*Attorney, Agent, or Firm*—Banner & Witcoff, Ltd.

[57] ABSTRACT

Sulfonamide-containing hydroxyethylamine compounds are effective as retroviral protease inhibitors, and in particular as inhibitors of HIV protease.

77 Claims, No Drawings

5,760,064

SULFONYLALKANOYLAMINO HYDROXYETHYLAMINO SULFANAMIDES USEFUL AS RETROVIRAL PROTEASE INHIBITORS

RELATED APPLICATION

This application is a continuation of application Ser. No. 08/587,688 filed on Jan. 17, 1996, now U.S. Pat. No. 5,639,769, which was a divisional of application Ser. No. 08/110,913 filed Aug. 24, 1993, now U.S. Pat. No. 5,521, 714, which was a continuation-in-part of application Ser. No. 07/935,071, filed Aug. 25, 1992 now abandoned.

BACKGROUND OF THE INVENTION

1. Field of the Invention

The present invention relates to retroviral protease inhibitors and, more particularly, relates to novel compounds and a composition and method for inhibiting retroviral proteases. This invention, in particular, relates to sulfonamide-containing hydroxyethylamine protease inhibitor compounds, a composition and method for inhibiting retroviral proteases such as human immunodeficiency virus (HIV) protease and for treating a retroviral infection, e.g., an HIV infection. The subject invention also relates to processes for making such compounds as well as to intermediates useful in such processes.

2. Related Art

During the replication cycle of retroviruses, gag and gag-pol gene products are translated as proteins. These proteins are subsequently processed by a virally encoded protease (or proteinase) to yield viral enzymes and structural proteins of the virus core. Most commonly, the gag precursor proteins are processed into the core proteins and the pol precursor proteins are processed into the viral enzymes, e.g., reverse transcriptase and retroviral protease. It has been shown that correct processing of the precursor proteins by the retroviral protease is necessary for assembly of infectious virons. For example, it has been shown that frameshift mutations in the protease region of the pol gene of HIV prevents processing of the gag precursor protein. It has also been shown through site-directed mutagenesis of an aspartic acid residue in the HIV protease that processing of the gag precursor protein is prevented. Thus, attempts have been made to inhibit viral replication by inhibiting the action of retroviral proteases.

Retroviral protease inhibition may involve a transition-state mimetic whereby the retroviral protease is exposed to a mimetic compound which binds to the enzyme in competition with the gag and gag-pol proteins to thereby inhibit replication of structural proteins and, more importantly, the retroviral protease itself. In this manner, retroviral replication proteases can be effectively inhibited.

Several classes of compounds have been proposed, particularly for inhibition of proteases, such as for inhibition of HIV protease. Such compounds include hydroxyethylamine isosteres and reduced amide isosteres. See, for example, EP O 346 847; EP O 342,541; Roberts et al, "Rational Design of Peptide-Based Proteinase Inhibitors," *Science*, 248, 358 (1990); and Erickson et al, "Design Activity, and 2.8 Å Crystal Structure of a $C_2$ Symmetric Inhibitor Complexed to HIV-1 Protease," *Science*, 249, 527 (1990).

Several classes of mimetic compounds are known to be useful as inhibitors of the proteolytic enzyme renin. See, for example, U.S. Pat. No. 4,599,198; U.K. 2,184,730; G.B. 2,209,752; EP O 264 795; G.B. 2,200,115 and U.S. SIR H725. Of these, G.B. 2,200,115, GB 2,209,752, EP O 264,795, U.S. SIR H725 and U.S. Pat. No. 4,599,198 disclose urea-containing hydroxyethylamine renin inhibitors. G.B. 2,200,115 also discloses sulfamoyl-containing hydroxyethylamine renin inhibitors and EP 0264795 discloses certain sulfonamide-containing hydroxyethylamine renin inhibitors. However, it is known that, although renin and HIV proteases are both classified as aspartyl proteases, compounds which are effective renin inhibitors generally cannot be predicted to be effective HIV protease inhibitors.

BRIEF DESCRIPTION OF THE INVENTION

The present invention is directed to virus inhibiting compounds and compositions. More particularly, the present invention is directed to retroviral protease inhibiting compounds and compositions, to a method of inhibiting retroviral proteases, to processes for preparing the compounds and to intermediates useful in such processes. The subject compounds are characterized as sulfonylalkanoylamino hydroxyethylamino sulfonamide inhibitor compounds.

DETAILED DESCRIPTION OF THE INVENTION

In accordance with the present invention, there is provided a retroviral protease inhibiting compound of the formula:

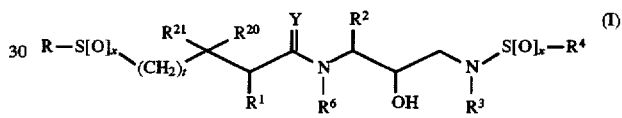

or a pharmaceutically acceptable salt, prodrug or ester thereof wherein:

R represents hydrogen, alkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminocarbonylalkyl, aminoalkylcarbonylalkyl, aminoalkyl, alkylcarbonylalkyl, aryloxyalkylcarbonylalkyl, aralkoxycarbonylalkyl radicals and mono- and disubstituted aminocarbonylalkyl, aminoalkylcarbonylalkyl and aminoalkyl radicals wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted radical, said substituents along with the nitrogen atom to which they are attached, form a heterocycloalkyl or a heteroaryl radical;

each x independently represents 0, 1 or 2;

t represents either 0 or 1;

$R^1$, $R^{20}$ and $R^{21}$ independently represent hydrogen, $-CH_2SO_2NH_2$, $-_{CH2}CO_2CH_3$, $-CO_2CH_3$, $-CONH_2$, $-CH_2C(O)NHCH_3$, $-C(CH_3)_2(SH)$, $-C(CH_3)_2(SCH_3)$, $-C(CH_3)_2(S[O]CH_3)$, $-C(CH_3)_2(S[O]_2CH_3)$, alkyl, haloalkyl, alkenyl, alkynyl and cycloalkyl radicals, and amino acid side chains selected from asparagine, S-methyl cysteine and the sulfoxide (SO) and sulfone ($SO_2$) derivatives thereof, isoleucine, allo-isoleucine, alanine, leucine, tert-leucine, phenylalanine, ornithine, histidine, norleucine, glutamine, threonine, glycine, allo-threonine, serine, O-alkyl serine, aspartic acid, beta-cyano alanine and valine side chains; $R^2$ represents alkyl, aryl, cycloalkyl, cycloalkylalkyl and aralkyl radicals, which radicals are

3 optionally substituted with a group selected from —NO$_2$, CN, —C≡N,CF$_3$, —OR$^9$, —SR$^9$, haloalkyl and halogen and alkyl radicals, wherein R$^9$ represents hydrogen and alkyl radicals;

R$^3$ represents hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

R$^4$ represents radicals as defined by R$^3$, excluding hydrogen;

Y represents O,S and NR$^{15}$ wherein R$^{15}$ represents hydrogen and radicals as defined for R$^3$; and R$^6$ represents hydrogen, and alkyl radicals.

A preferred class of retroviral inhibitor compounds of the present invention are those represented by the formula:

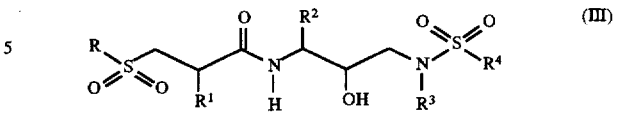

or a pharmaceutically acceptable salt, prodrug or ester thereof, preferably wherein the absolute stereochemistry about the hydroxy group is designated as (R);

R represents alkyl, alkenyl, alkynyl, cycloalkyl, hydroxyalkyl, cycloalkylalkyl, heterocycloalkyl, heterocycloalkylalkyl, alkoxyalkyl, aryl, heteroaryl, aralkyl, heteroaralkyl, aminocarbonylalkyl, aminoalkylcarbonylalkyl, alkylcarbonylalkyl, aryloxyalkylcarbonyl, and aralkoxycarbonylalkyl radicals;

R$^1$, R$^{20}$ and R$^{21}$ independently represent hydrogen, —CH$_2$SO$_2$NH$_2$, —$_{CH2}$CO$_2$CH$_3$, —CO$_2$CH$_3$, —CONH$_2$, —CH$_2$C(O)NHCH$_3$, —C(CH$_3$)$_2$(SCH$_3$), —C(CH$_3$)$_2$(S[O]CH$_3$), —C(CH$_3$)$_2$(S[O]$_2$CH$_3$), alkyl, haloalkyl, alkenyl, alkynyl and cycloalkyl radicals, and amino acid side chains selected from asparagine, S-methyl cysteine and the sulfoxide (SO) and sulfone (SO$_2$) derivatives thereof, isoleucine, allo-isoleucine, alanine, leucine, tert-leucine, phenylalanine, ornithine, histidine, norleucine, glutamine, threonine, glycine, allo-threonine, serine, O-methyl serine, aspartic acid, beta-cyano alanine and valine side chains;

R$^2$ represents alkyl, aryl, cycloalkyl, cycloalkylalkyl, and aralkyl radicals, which radicals are optionally substituted with a group selected from alkyl and halogen radicals, NO$_2$, CN, —C≡N,CF$_3$, OR$^9$ and SR$^9$ wherein R$^9$ represents hydrogen and alkyl radicals, and halogen radicals;

R$^3$ represents alkyl, haloalkyl, alkenyl, hydroxyalkyl, alkoxyalkyl, cycloalkyl, cycloalkylalkyl, heterocycloalkyl, heterocycloalkylalkyl, aryl, heteroaryl, aralkyl and heteroaralkyl radicals; and R$^4$ represents radicals as defined by R$^3$ except for hydrogen;

t represents 0 or 1;

Y represents O, S, and NR$^{15}$ wherein R$^{15}$ represents hydrogen and radicals as defined for R$^3$. Preferably, Y represents O.

4

A preferred class of compounds within Formula I are those represented by the formula:

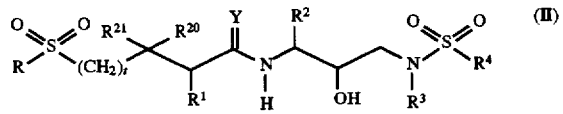

or a pharmaceutically acceptable salt, prodrug or ester thereof wherein R, R$^1$, R$^2$, R$^3$, and R$^4$ are as defined above, with respect to Formula (II).

As utilized herein, the term "alkyl", alone or in combination, means a straight-chain or branched-chain alkyl radical containing from 1 to about 10, preferably from 1 to about 8, carbon atoms. Examples of such radicals include methyl, ethyl, n-propyl, isopropyl, n-butyl, isobutyl, sec-butyl, tert-butyl, pentyl, isoamyl, hexyl, octyl and the like. The term "alkenyl", alone or in combination, means a straight-chain or branched-chain hydrocarbon radial having one or more double bonds and containing from 2 to about 18 carbon atoms preferably from 2 to about 8 carbon atoms. Examples of suitable alkenyl radicals include ethenyl, propenyl, 1,4-butadienyl and the like. The term alkynyl, alone or in combination, means a straight-chain hydrocarbon radical having one or more triple bonds and containing from 2 to about 10 carbon atoms. Examples of alkynyl radicals include ethynyl, propynyl, propargyl and the like. The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkyl", alone or in combination, means a saturated or partially saturated monocyclic, bicyclic or tricyclic alkyl radical wherein each cyclic moiety contains from about 3 to about 8 carbon atoms. The term "cycloalkylalkyl" means an alkyl radical as defined above which is substituted by a cycloalkyl radical containing from about 3 to about 8, preferably from about 3 to about 6, carbon atoms. Examples of such cycloalkyl radicals include cyclopropyl, cyclobutyl, cyclopentyl, cyclohexyl and the like. The term "aryl", alone or in combination, means a phenyl or naphthyl radical which optionally carries one or more substituents selected from alkyl, alkoxy, halogen, hydroxy, amino, nitro, cyano, haloalkyl and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like. The term "aralkyl", alone or in combination, means an alkyl radical as defined above in which one hydrogen atom is replaced by an aryl radical as defined above, such as benzyl, 2-phenylethyl and the like. The term "aralkoxy carbonyl", alone or in combination, means a radical of the formula —C(O)—O-aralkyl in which the term "aralkyl" has the significance given above. An example of an aralkoxycarbonyl radical is benzyloxycarbonyl. The term "aryloxy" means a radical of the formula aryl-O— in which the term aryl has the significance given above. The term "alkanoyl", alone or in combination, means an acyl radical derived from an alkanecarboxylic acid, examples of which include acetyl, propionyl, butyryl, valeryl, 4-methylvaleryl, and the like. The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkanoylamino, such as 1,2,3,4-tetrahydro-2-naphthoyl,2-acetamido-1,2,3,4-tetrahydro-2-naphthoyl. The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl,4-methoxyhydrocinnamoyl, and the like. The term "aroyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl)benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like. The heterocyclyl or heterocycloalkyl portion of a heterocyclylcarbonyl, heterocyclyloxycarbonyl, heterocyclylalkoxycarbonyl, or heterocyclyalkyl group or the like is a saturated or partially unsaturated monocyclic, bicyclic or tricyclic heterocycle which contains one or more hetero atoms selected from nitrogen, oxygen and sulphur, which is optionally substituted on one or more carbon atoms by halogen, alkyl, alkoxy, oxo, and the like, and/or on a secondary nitrogen atom (i.e., —NH—) by alkyl, aralkoxycarbonyl, alkanoyl, phenyl or phenylalkyl or on a tertiary nitrogen atom (i.e. =N—) by oxido and which is attached via a carbon atom. The heteroaryl portion of a heteroaroyl, heteroaryloxycarbonyl, or a heteroaralkoxy carbonyl group or the like is an aromatic monocyclic, bicyclic, or tricyclic heterocycle which contains the hetero atoms and is optionally substituted as defined above with respect to the definition of heterocyclyl. Examples of such heterocyclyl and heteroaryl groups are pyrrolidinyl, piperidinyl, piperazinyl, morpholinyl, thiamorpholinyl, pyrrolyl, imidazolyl (e.g., imidazol 4-yl, 1-benzyloxycarbonylimidazol-4-yl, etc.), pyrazolyl, pyridyl, pyrazinyl, pyrimidinyl, furyl, thienyl, triazolyl, oxazolyl, thiazolyl, indolyl (e.g., 2-indolyl, etc.), quinolinyl, (e.g., 2-quinolinyl, 3-quinolinyl, 1-oxido-2-quinolinyl, etc.), isoquinolinyl (e.g., 1-isoquinolinyl, 3-isoquinolinyl, etc.), tetrahydroquinolinyl (e.g., 1,2,3,4-tetrahydro-2-quinolyl, etc.), 1,2,3,4-tetrahydroisoquinolinyl (e.g., 1,2,3,4-tetrahydro-1-oxo-isoquinolinyl, etc.), quinoxalinyl, β-carbolinyl, 2-benzofurancarbonyl, 1-,2-,4- or 5-benzimidazolyl, and the like. The term "cycloalkylalkoxycarbonyl" means an acyl group derived from a cycloalkylalkoxycarboxylic acid of the formula cycloalkylalkyl-O—COOH wherein cycloalkylalkyl has the significance given above. The term "aryloxyalkanoyl" means an acyl radical of the formula aryl-O-alkanoyl wherein aryl and alkanoyl have the significance given above. The term "heterocyclyloxycarbonyl" means an acyl group derived from heterocyclyl-O—COOH wherein heterocyclyl is as defined above. The term "heterocyclylalkanoyl" is an acyl radical derived from a heterocyclyl-substituted alkane carboxylic acid wherein heterocyclyl has the significance given above. The term "heterocyclylalkoxycarbonyl" means an acyl radical derived from a heterocyclyl-substituted alkane-O—COOH wherein heterocyclyl has the significance given above. The term "heteroaryloxycarbonyl" means an acyl radical derived from a carboxylic acid represented by heteroaryl-O—COOH wherein heteroaryl has the significance given above. The term "aminocarbonyl" alone or in combination, means an amino-substituted carbonyl (carbamoyl) group derived from an amino-substituted carboxylic acid wherein the amino group can be a primary, secondary or tertiary amino group containing substituents selected from hydrogen, and alkyl, aryl, aralkyl, cycloalkyl, cycloalkylalkyl radicals and the like. The term "aminoalkanoyl" means an acyl group derived from an amino-substituted alkanecarboxylic acid wherein the amino group can be a primary, secondary or tertiary amino group containing substituents selected from hydrogen, and alkyl, aryl, aralkyl, cycloalkyl, cycloalkylalkyl radicals and the like. The term "halogen" means fluorine, chlorine, bromine or iodine. The term "leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

Procedures for preparing the compounds of Formula I are set forth below. It should be noted that the general procedure is shown as it relates to preparation of compounds having the specified stereochemistry, for example, wherein the absolute stereochemistry about the hydroxyl group is designated as (R). However, such procedures are generally applicable to those compounds of opposite configuration, e.g., where the stereochemistry about the hydroxyl group is (S). In addition, the compounds having the (R) stereochemistry can be utilized to produce those having the (S) stereochemistry, and vice versa. For example, a compound having the (R) stereochemistry can be inverted to the (S) stereochemistry using well-known methods.

Preparation of Compounds of Formula I

The compounds of the present invention represented by Formula II above can be prepared utilizing the following general procedure. An N-protected chloroketone derivative of an amino acid having the formula:

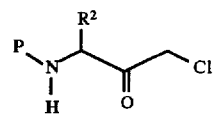

wherein P represents an amino protecting group, and R² is as defined above, is reduced to the corresponding alcohol utilizing an appropriate reducing agent. Suitable amino protecting groups are well known in the art and include carbobenzoxy, butyryl, t-butoxycarbonyl, acetyl, benzoyl and the like. A preferred amino protecting group is carbobenzoxy. A preferred N-protected chloroketone is N-benzyloxycarbonyl-L-phenylalanine chloromethyl ketone. A preferred reducing agent is sodium borohydride. The reduction reaction is conducted at a temperature of from −10° C. to about 25° C., preferably at about 0° C., in a suitable solvent system such as, for example, tetrahydrofuran, and the like. The N-protected chloroketones are commercially available, e.g., such as from Bachem, Inc., Torrance, Calif. Alternatively, the chloroketones can be prepared by the procedure set forth in S. J. Fittkau, *J. Prakt. Chem.*, 315, 1037 (1973), and subsequently N-protected utilizing procedures which are well known in the art.

The halo alcohol can be used directly, as described below, or, preferably, is then reacted, preferably at room temperature, with a suitable base in a suitable solvent system to produce an N-protected amino epoxide of the formula:

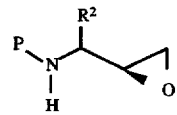

wherein P and R² are as defined above. Suitable solvent systems for preparing the amino epoxide include ethanol, methanol, isopropanol, tetrahydrofuran, dioxane, and the like including mixtures thereof. Suitable bases for producing the epoxide from the reduced chloroketone include potassium hydroxide, sodium hydroxide, potassium t-butoxide, DBU and the like. A preferred base is potassium hydroxide.

Alternatively, a protected amino epoxide can be prepared starting with an L-amino acid which is reacted with a suitable amino-protecting group in a suitable solvent to produce an amino-protected L-amino acid ester of the formula:

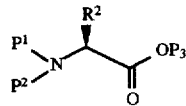

wherein $P^1$ and $P^2$ independently represent hydrogen, benzyl and amino-protecting groups (as defined above with respect to P), provided that $P^1$ and $P^2$ are not both hydrogen; $P^3$ is a carboxyl protecting group (such as methyl, ethyl, tertiary-butyl, benzyl and the like); and $R^2$ is as defined above.

The amino-protected L-amino acid ester is then reduced, to the corresponding alcohol. For example, the amino-protected $L_4$-amino acid ester can be reduced with diisobutylaluminum hydride at $-78°$ C. in a suitable solvent such as toluene. The resulting alcohol is then converted, for example, by way of a Swern oxidation, to the corresponding aldehyde of the formula:

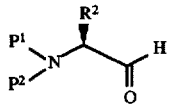

wherein $P^1$, $P^2$ and $R^2$ are as defined above. Thus, a dichloromethane solution of the alcohol is added to a cooled ($-75°$ to $-68°$ C.) solution of oxalyl chloride in dichloromethane and DMSO in dichloromethane and stirred for 35 minutes.

The aldehyde resulting from the Swern oxidation is then reacted with a halomethyllithium reagent, which reagent is generated in situ by reacting an alkyllithium or arylithium compound with a dihalomethane represented by the formula $X^1CH_2X^2$ wherein $X^1$ and $X^2$ independently represent I, Br or Cl. For example, a solution of the aldehyde and chloroiodomethane in THF is cooled to $-78°$ C. and a solution of n-butyllithium in hexane is added. The resulting product is a mixture of diastereomers of the corresponding amino-protected epoxides of the formulas:

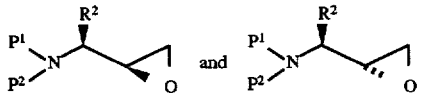

The diastereomers can be separated e.g., by chromatography, or, alternatively, once reacted in subsequent steps the diastereomeric products can be separated. For compounds having the (S) stereochemistry, a D-amino acid can be utilized in place of the L-amino acid.

The amino epoxide is then reacted, in a suitable solvent system, with an equal amount, or preferably an excess of, a desired amine of the formula:

$R^3NH_2$ wherein $R^3$ is hydrogen or is as defined above. The reaction can be conducted over a wide range of temperatures, e.g., from about 10° C. to about 100° C., but is preferably, but not necessarily, conducted at a temperature at which the solvent begins to reflux. Suitable solvent systems include protic, non-protic and dipolar aprotic organic solvents such as, for example, those wherein the solvent is an alcohol, such as methanol, ethanol, isopropanol, and the like, ethers such as tetrahydrofuran, dioxane and the like, and toluene, N,N-dimethylformamide, dimethyl sulfoxide, and mixtures thereof. A preferred solvent is isopropanol. Exemplary amines corresponding to the formula $R^3NH_2$ include benzyl amine, isobutylamine, n-butyl amine, isopentyl amine, isoamylamine, cyclohexanemethyl amine, naphthylene methyl amine and the like. The resulting product is a 3-(N-protected amino)-3-($R^2$)-1-($NHR^3$)-propan-2-ol derivative (hereinafter referred to as an amino alcohol) represented by the formulas:

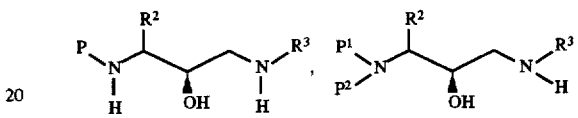

wherein P, P1, P2, $R^2$ and $R^3$ are as described above. Alternatively, a haloalcohol can be utilized in place of the amino epoxide.

The amino alcohol defined above is then reacted in a suitable solvent with a sulfonyl chloride ($R^4SO_2Cl$) or sulfonyl anhydride in the presence of an acid scavenger. Suitable solvents in which the reaction can be conducted include methylene chloride, tetrahydrofuran and the like. Suitable acid scavengers include triethylamino, pyridine and the like. Preferred sulfonyl chlorides are methane sulfonyl chloride and benzenesulfonyl chloride. The resulting sulfonamide derivative can be represented, depending on the epoxide utilized, by the formulas

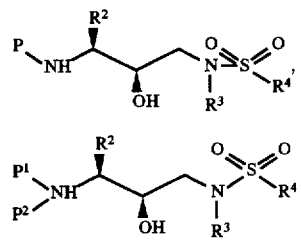

wherein P, $P^1$, $P^2$, $R^2$, $R^3$ and $R^4$ are as defined above. These intermediates are useful for preparing inhibitor compounds of the present invention and are also active inhibitors of retroviral proteases.

The sulfonyl halides of the formula $R^4SO_2X$ can be prepared by the reaction of a suitable Grignard or alkyl lithium reagent with sulfuryl chloride, or sulfur dioxide followed by oxidation with a halogen, preferably chlorine. Also, thiols may be oxidized to sulfonyl chlorides using chlorine in the presence of water under carefully controlled conditions. Additionally, sulfonic acids may be converted to sulfonyl halides using reagents such as $PCl_5$, and also to anhydrides using suitable dehydrating reagents. The sulfonic acids may in turn be prepared using procedures well known in the art. Such sulfonic acids are also commercially available.

In place of the sulfonyl halides, sulfinyl halides ($R^4SOCl$) and sulfenyl halides ($R^4SCl$) can be utilized to produce compounds wherein the —$SO_2$— moiety is replaced by —SO— and —S—, respectively.

Following preparation of the sulfonamide derivative, the amino protecting group P is removed, or the groups $P^1$ and P² are removed, under conditions which will not affect the remaining portion of the molecule. These methods are well known in the art and include acid hydrolysis, hydrogenolysis and the like. A preferred method involves removal of the protecting group, e.g., removal of a carbobenzoxy group, by hydrogenolysis utilizing palladium on carbon in a suitable solvent system such as an alcohol, acetic acid, and the like or mixtures thereof. Where the protecting group is a t-butoxycarbonyl group, it can be removed utilizing an inorganic or organic acid, e.g., HCl or trifluoroacetic acid, in a suitable solvent system, e.g., dioxane or methylene chloride. The resulting product is the amine salt derivative. Where the protecting group is a benzyl radical, it can be removed by hydrogenolysis. Following neutralization of the salt, the amine is then reacted with a sulfone of the formula:

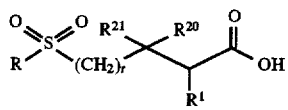

Wherein R, R¹, R²⁰, R²¹ and t are as defined above. The sulfone is prepared according to the following procedure.

A mercaptan of the formula RSH is reacted with a substituted methacrylate of the formula:

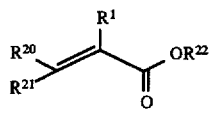

by way of a Michael Addition. The Michael Addition is conducted in a suitable solvent and in the presence of a suitable base, to produce the corresponding thiol derivative represented by the formula:

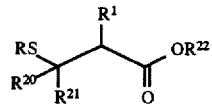

wherein R and R¹ represent radicals defined above; R²⁰ and R²¹ represent hydrogen and radicals as defined for R¹; and R²² represents a carboxyl protecting group such as methyl, ethyl, benzyl, t-butyl or the like. Suitable solvents in which the Michael Addition can be conducted include protic, non-protic and dipolar aprotic organic solvents, e.g., alcohols such as, for example, methanol, ethanol, butanol and the like, as well as ethers, e.g., THF, and acetonitrile, DMF, DMSO, and the like, including mixtures thereof. Suitable bases include Group I metal alkoxides such as, for example sodium methoxide, sodium ethoxide, sodium butoxide and the like as well as Group I metal hydrides, such as sodium hydride, including mixtures thereof.

The thiol derivative is converted into the corresponding sulfone or sulfoxide of the formula:

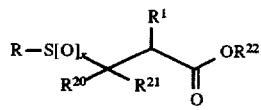

by oxidizing the thiol derivative with a suitable oxidation agent in a suitable solvent. Suitable oxidation agents include, for example, hydrogen peroxide, sodium meta-perborate, oxone (potassium peroxy monosulfate), meta-chloroperoxybenzoic acid, periodic acid and the like, including mixtures thereof. Suitable solvents include acetic acid (for sodium meta-perborate) and, for other peracids, ethers such as THF and dioxane, and acetonitrile, DMF and the like, including mixtures thereof.

The sulfone is then converted to the corresponding free acid of the formula:

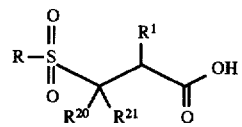

One method involves utilizing a suitable base, e.g., lithium hydroxide, sodium hydroxide, and the like, including mixtures thereof, in a suitable solvent, such as, for example, THF, water, acetonitrile, DMF, DMSO, methylene chloride and the like, including mixtures thereof. Other methods which can be used for deprotection depend on the nature of R²². For example, when R²² is a tertiary-butyl group, one can use a strong acid such as hydrochloric acid or trifluoroacetic acid. When R²² is a benzyl group, it can be removed via hydrogenolysis.

The free acid is then coupled, utilizing procedures well known in the art, to the sulfonamide derivative, or analog thereof, of an amino alcohol which is described above. The resulting product is a compound represented by Formula I.

Alternatively, one can couple the sulfonamide isostere to the commercially available acid,

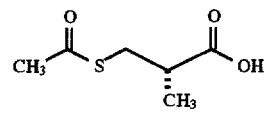

remove the thioacetyl group with a suitable base, such as hydroxide, or an amine, such as ammonia, and then react the resulting thiol with an alkylating agent, such as an alkyl halide, tosylate or mesylate to afford compounds at the following structure:

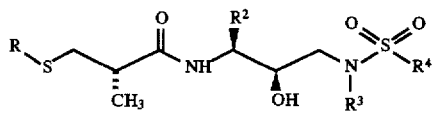

The sulfur can then be oxidized to the corresponding sulfone or sulfoxide using suitable oxidizing agents, as described above, to afford the desired compounds of the following structure:

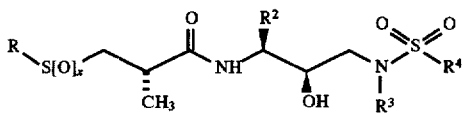

Alternatively, to prepare compounds of Formula I, a substituted methacrylate of the formula:

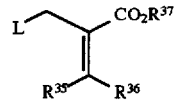

wherein L represents a leaving group as previously defined, R³⁵ and R³⁶ represent hydrogen and radicals as defined for $R^1$, and $R^{37}$ represents alkyl, aralkyl, cycloalkyl and cycloalkylalkyl radicals, is reacted with a suitable sulfonating agent, such as, for example, a sulfinic acid represented by the formula $RSO_2M$, wherein R represents radicals as defined above and M represents a metal adapted to form a salt of the acid, e.g., sodium, to produce the corresponding sulfone represented by the formula:

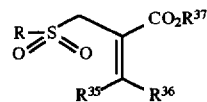

wherein R, $R^{35}$, $R^{36}$ and $R^{37}$ are as defined above. The sulfone is then hydrolyzed in the presence of a suitable base, such as lithium hydroxide, sodium hydroxide and the like, to the compound represented by the formula:

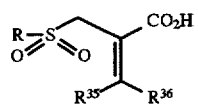

wherein R, $R^{35}$ and $R^{36}$ represent radicals as defined above. The resulting compound is then asymmetrically hydrogenated utilizing an asymmetric hydrogenation catalyst such as, for example, a ruthenium-BINAP complex, to produce the reduced product, substantially enriched in the more active isomer, represented by the formula:

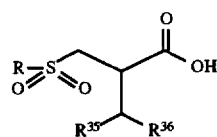

wherein R, $R^{35}$ and $R^{36}$ represent radicals as defined above. Where the more active isomer has the R-stereochemistry, a Ru(R-BINAP) asymmetric hydrogenation catalyst can be utilized. Conversely, where the more active isomer has the S-sterochemistry, a Ru(S-BINAP) catalyst can be utilized. Where both isomers are active, or where it is desired to have a mixture of the two diastereomers, a hydrogenation catalyst such as platinum, or palladium, on carbon can be utilized to reduce the above compound. The reduced compound is then coupled to the sulfonamide isostere, as described above, to produce compounds of Formula II.

Alternatively, an acid or a derivative of an acid properly substituted with a leaving group (discussed above) can be treated with a Mercaptan and a base (see above) to provide an organic sulfide. Acid derivatives are defined above. The resulting sulfide can be oxidized to the corresponding sulfoxide or sulfone by methods previously discussed.

A preferred method to prepare 2(S)-methyl-3-(methylsulfonyl)propionic acid is as follows. Beginning with the commercially available compounds of the following structure;

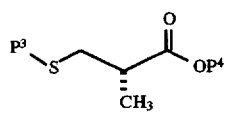

Where $P^3$ is a protecting group for sulfur, preferably a benzoyl or acetyl, and $P^4$ is either hydrogen or a carboxylic acid protecting group such as methyl, ethyl, tertiary-butyl, benzyl and the like. Preferably, $P^4$ is tertiary-butyl. The sulfur protecting group $P^3$ can be selectively removed using methods known to those skilled in the art. For example, where P3 is either benzoyl or acetyl, it can be removed by treatment with an inorganic base or an amine, preferably ammonia, in an appropriate solvent such as methanol, ethanol, isopropanol, toluene or tetrahydrofuran. The preferred solvent is methanol. This provides a compound of the following structure;

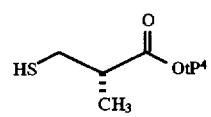

which can be alkylated on the sulfur with a compound of the structure

RX

Where R is as defined above, and X is an appropriate leaving group, such as a halide (chloride, bromide, iodide), mesylate, tosylate or triflate. The reaction is performed in the presence of a suitable base, such as triethylamine, diisopropylethylamine, 1,8-diazabicyclo[5.4.0] undec-7-ene (DBu) and the like, in a suitable solvent such as toluene, tetrahydrofuran, or methylene chloride. The preferred base is DBU and the preferred solvent is toluene. Where R is a methyl group, RX can be methyl chloride, methyl bromide, methyl iodide, or dimethyl sulfate. Preferably RX is methyl iodide. The product of the reaction is a compound of the structure;

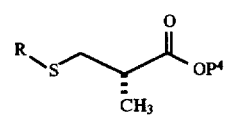

The sulfur can then be oxidized to either the sulfoxide or sulfone using methods known to those skilled in the art. Suitable oxidizing agents are meta-chloroperbenzoic acid, hydrogen peroxide, sodium perborate and the like. Appropriate solvents are methylene chloride, toluene, acetic acid, propionic acid and the like. The preferred method is using hydrogen peroxide or sodium perborate in acetic acid. The sulfone product has the structure;

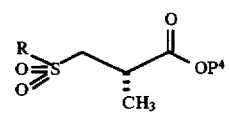

The carboxylic acid protecting group $P^4$ can then be removed using methods well known to those in the art. For example, when $P^4$ is a tertiary-butyl group, it can be removed by treatment with an acid, such as hydrochloric acid or trifluoracetic acid. The preferred method is using 4N hydrochloric acid in dioxane. This provides the desired final compound of the structure;

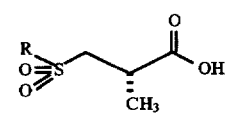

It is envisioned that one skilled in the art could utilize variations on the synthetic sequence such as the use of different protecting groups for the sulfur ($P^3$) or for the carboxylic acid (P⁴), and different reagents to carry out the same transformations.

It is contemplated that for preparing compounds of the Formulas having $R^6$, the compounds can be prepared following the procedure set forth above and, prior to coupling the sulfonamide derivative or analog thereof to the sulfone carried through a procedure referred to in the art as reductive amination. Thus, a sodium cyanoborohydride and an appropriate aldehyde or ketone can be reacted with the sulfonamide derivative compound or appropriate analog at room temperature in order to reductively aminate any of the compounds of Formulas I–III. It is also contemplated that where $R^3$ of the amino alcohol intermediate is hydrogen, the inhibitor compounds can be prepared through reductive amination of the final product of the reaction between the amino alcohol and the amine or at any other stage of the synthesis for preparing the inhibitor compounds.

Contemplated equivalents of the general formulas set forth above for the antiviral compounds and derivatives as well as the intermediates are compounds otherwise corresponding thereto and having the same general properties wherein one or more of the various R groups are simple variations of the substituents as defined therein, e.g., wherein R is a higher alkyl group than that indicated. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received without purification. All proton and carbon NMR spectra were obtained on either a Varian VXR-300 or VXR-400 nuclear magnetic resonance spectrometer.

EXAMPLE 1A

Preparation of N[3(S)-benzyloxycarbonylamino-2 (R)-hydroxy-4-phenylbutyl]-N-isoamylamine.

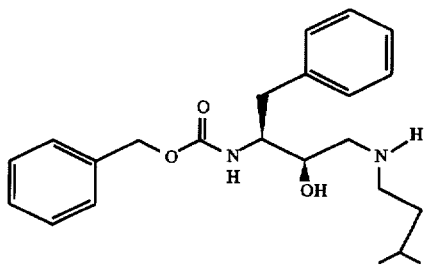

PART A

To a solution of N-benzyloxycarbonyl-L-phenylalanine chloromethyl ketone (75 g, 0.2 mol) in a mixture of 800 mL of methanol and 800 mL of tetrahydrofuran was added sodium borohydride (13.17 g, 0.348 mol, 1.54 equiv.) over 100 min. The solution was stirred at room temperature for 2 h and then concentrated in vacuo. The residue was dissolved in 1000 mL of ethyl acetate and washed with 1N $KHSO_4$, saturated aqueous $NaHCO_3$, saturated aqueous NaCl, dried over anhyd $MgSO_4$, filtered and concentrated in vacuo to give an oil. The crude product was dissolved in 1000 mL of hexanes at 60° C. and allowed to cool to room temperature whereupon crystals formed that were isolated by filtration and washed with copious amounts of hexanes. This solid was then recrystallized from hot ethyl acetate and hexanes to provide 32.3 g 43% of N-benzyloxycarbonyl-3(S)-amino-1-chloro-4-phenyl-2(S)-butanol, mp 150°–151° C., FAB MS: $MLi^+=340$.

PART B

A solution of potassium hydroxide (6.52 g, 0.116 mol, 1.2 equiv.) in 970 mL of absolute ethanol was treated with N-benzyloxycarbonyl-3(S)-amino-1-chloro-4-phenyl-2(S)-butanol (32.3 g, 0.097 mol). This solution was stirred at room temperature for 15 min and then concentrated in vacuo to give a white solid. The solid was dissolved in dichloromethane and washed with water, dried over anhyd $MgSO_4$, filtered and concentrated in vacuo to give a white solid. The solid was crystallized from hexanes and ethyl acetate to give 22.3 g, 77% of N-benzyloxycarbonyl-3(S)-amino-1,2(S)epoxy-4-phenylbutane, mp 102°–103° C., FAB MS: $MH^+=298$.

PART C

A solution of N-benzyloxycarbonyl-3(S)-amino-1,2(S) epoxy-4-phenylbutane (11.54 g, 38.81 mmol) and isoamylamine (66.90 g, 0.767 mol, 19.9 equivalents) in 90 mL of isopropyl alcohol was heated to reflux for 3.1 h. The solution was cooled to room temperature and partially concentrated in vacuo and the remaining solution poured into 200 mL of stirring hexanes whereupon the product crystallized from solution. The product was isolated by filtration and air dried to give 11.76 g, 79% of N[[3(S)-phenylmethylcarbamoyl) amino-2(R)-hydroxy-4-phenylbutyl]N-[(3-methylbutyl)] amine, mp 118°–122° C., FAB MS: $MH^+=385$.

EXAMPLE 1B

Preparation of N-[[3S-(phenylmethylcarbamoyl) amino]-2R-hydroxy-4-phenyl]-1-[(2-methylpropyl) amino-2-(1,1-dimethylethoxyl)carbonyl]butane

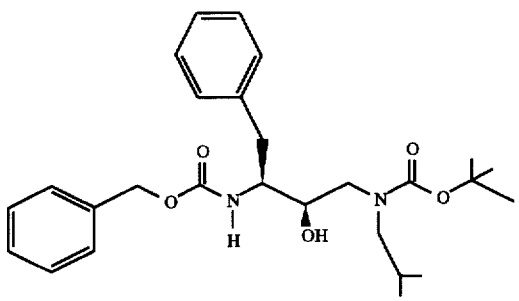

To a solution of 7.51 g (20.3 mmol) of N-[[3S-(phenylmethylcarbamoyl)amino]-2R-hydroxy-4-phenylbutyl]-N-(2-methylpropyl)]amine in 67 mL of anhydrous tetrahydrofuran was added 2.25 g (22.3 mmol) of triethylamine. After cooling to 0 C, 4.4 g (20.3 mmol) of di-tert-butyldicarbonate was added and stirring continued at room temperature for 21 hours. The volatiles were removed in vacuo, ethyl acetate added, then washed with 5% citric acid, saturated sodium bicarbonate, brine, dried over magnesium sulfate, filtered and concentrated to afford 9.6 g of crude product. Chromatography on silica gel using 30% ethyl acetate/hexane afforded 8.2 g of pure N-[[3S-(phenylmethylcarbamoyl)amino]-2R-hydroxy-4-phenyl]-1-[2-methylpropyl)amino-2-(1,1-dimethylethoxyl)carbonyl] butane, mass spectrum m/e=477 (M+Li).

EXAMPLE 2

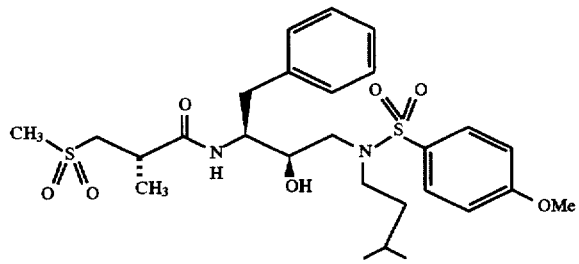

Preparation of Propanamide, N-[2-hydroxy-3-[3-methylbutyl)(4-methoxyphenylsulfonyl)amino]-1-(phenylmethyl)propyl]-2-methyl-3-(methylsulfonyl)-[1S-[1R*(R*),2S*]]-

PART A

A solution of the amino alcohol from Example 1, Part C (1.1515 g, 2.99 mmol), and triethylamine (313.5 mg, 3.10 mmol) in 15 mL of dichloromethane was treated with 4-methoxybenzenesulfonyl chloride (630.6 mg, 3.05 mmol) via syringe. The solution was stirred at room temperature for 40 min and then concentrated in vacuo. The residue was dissolved in ethyl acetate and washed with 1N $KHSO_4$, saturated aqueous $NaHCO_3$, brine, dried over anhyd $MgSO_4$, filtered and concentrated to give 1.5622 g, of a white foam. The crude product was purified by recrystallization from a mixture of hexanes and ethyl acetate to give 1.1047 g, 67% of pure product mp 95°–98° C. High resolution FAB Mass spectrum calc'd. for $C_{30}H_{38}N_2O_6S$: 555.2529. Found: 555.2559.

PART B

A solution of the product from Part A (970 mg, 1.68 mmol) in 30 mL of methanol was treated with 70 mg of 10% palladium on carbon catalyst and hydrogenated at 41 psig for 16 h at room temperature. The catalyst was removed by filtration and the filtrate concentrated in vacuo to give a clear oil that solidified upon standing, mp 81°–85° C., FAB MS; $MH^+$=421, 764.1 mg that was used directly in the next step.

PART C

A mixture of 2(S)-methyl-3-methylsulfonyl propionic acid (194 mg, 1.17 mmol), N-hydroxybenzotriazole (276 mg, 1.34 mmol), and 1-(3-dimethylaminopropyl)-3-ethylcarbodiimide hydrochloride (EDC) (256 mg, 1.34 mmol) was dissolved in 3.5 mL of dimethylformamide (DMF) and allowed to react for 30 min at 0° C. The amine from Part B (451.1 mg, 1.07 mmol) dissolved in 1.5 mL of DMF was added to the above mixture and stirred at room temperature for 16 h. The solution was then poured into 20 mL of saturated aqueous $NaHCO_3$ and extracted 4 times with ethyl acetate. The combined ethyl acetate extracts were washed with 5% aqueous citric acid, saturated aqueous $NaHCO_3$, brine, dried over anhyd $MgSO_4$, filtered and concentrated to give a clear oil that crystallized upon standing. The material was recrystallized from hexanes and ethyl acetate to give 517.6 mg, 85% of pure product with mp 125°–129° C. HRFAB MS; calc'd. for $C_{27}H_{40}N_2O_7S_2$: 569.2355. Found: 569.2397.

EXAMPLE 3

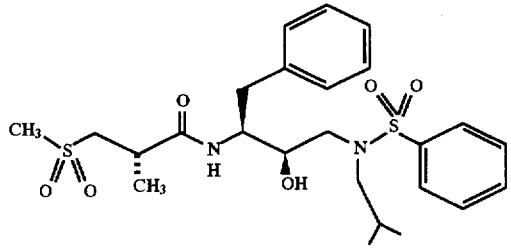

Preparation of propanamide, N-[2-hydroxy-3-[(2-methylpropyl) (phenylsulfonyl)amino]-1-((phenylmethyl)propyl]-2-methyl-3-(methylsulfonyl)-, [1S-[1R*(R*),2S*]]-

PART A

A solution of N-benzyloxycarbonyl-3(S)-amino-1,2-(S)-epoxy-4-phenyl butane (50.0 g, 0.168 mol) and isobutylamine (246 g, 3.24 mol, 20 equivalents) in 650 mL of isopropyl alcohol was heated to reflux for 1.25 hours. The solution was cooled to room temperature, concentrated in vacuo and then poured into 1 L of stirring hexane whereupon the product crystallized from solution. The product was isolated by filtration and air dried to give 57.56 g, 92% of N[3(S)-benzyloxycarbonylamino-2(R)-hydroxy-4-phenyl] N-isobutylamine, mp 108.0°–109.5° C., MH+m/z=371.

PART B

The amine from Part A (936.5 mg, 2.53 mmol) and triethylamine (288.5 mg, 2.85 mmol) was dissolved in 20 mL of dichloromethane and treated with benzenesulfonyl chloride (461 mg, 2.61 mmol). The solution was stirred at room temperature for 16 h and then concentrated in vacuo. The residue was dissolved in ethyl acetate and this solution was washed with 1N $KHSO_4$, saturated aqueous $NaHCO_3$, brine, dried over anhyd $MgSO_4$, filtered, and concentrated to give a clear oil 1.234 g. The oil was crystallized from a mixture of ether and hexanes, 729.3 mg, 56.5%, mp 95°–99° C., FAB MS; $MH^+$=511.

PART C

A solution of phenylmethyl [2(R)-hydroxy-3-[2-methylpropyl] (benzenesulfonyl) amino]1-S-(phenylmethyl) propyl carbamate (671.1 mg, 1.31 mmol) from Part B in 10 mL of methanol was hydrogenated over 50 mg of 10% palladium on carbon at 40 psig at room temperature for 15 h. The catalyst was removed by filtration through diatomaceous earth and the filtrate concentrated to give a white foam, 474.5 mg, 96%, FAB MS; MH$^+$=377, which was used directly in the next step without further purification.

PART D

A mixture of 2(S)methyl-3(methylsulfonyl) propionic acid (210.6 mg, 1.27 mmol), N-hydroxybenzotriazole (260.4 mg, 1.70 mmol) and EDC (259 mg, 1.35 mmol) in 3.5 mL of DMF was stirred at 0° C. for 0.5 h. The amine from Part C (474 mg, 1.15 mmol) dissolved in 2 mL of DMF was added to the above solution and stirred at room temperature for 16 h and then poured into 100 mL of 50% saturated aqueous NaHCO$_3$. The aqueous solution was extracted with ethyl acetate. The ethyl acetate solution was washed with 5% aqueous citric acid, saturated aqueous NaHCO$_3$, brine, dried over anhyd MgSO$_4$, filtered and concentrated to give a white foam, 560.5 mg which was crystallized from ethyl acetate and hexanes to provide 440.3 mg of pure product, mp 112°–116.5° C., HR FAB MS; Calc'd for $C_{25}H_{36}N_2O_6S_2$: 525.2093. Found: 525.2077

EXAMPLE 4

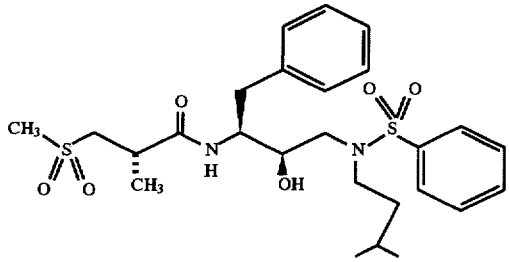

Preparation of propanamide, N-[2-hydroxy-3-[(3-methylbutyl) (phenylsulfonyl)amino]-1-(phenylmethyl)propyl]-2-methyl-3-(methylsulfonyl)-, [1S-[1R*(R*),2S*]]-

PART A

A mixture of N[3(S)-benzyloxycarbonylamino-2(R)-hydroxy-4-phenylbutyl]N-[(3-methylbutyl)]amine (Example 1, Part C) (3.89 g, 10.1 mmol) and triethylamine (1.02 g, 10.1 mmol) were dissolved in 25 mL of tetrahydrofuran (THF) and treated with a solution of di-tert-butylpyrocarbonate (2.21 g, 10.1 mmol) dissolved in 10 mL of THF. The solution was stirred at room temperature for 1.5 h and then concentrated in vacuo. The residue was dissolved in ethyl acetate and washed with 1N KHSO$_4$, saturated aqueous NaHCO$_3$, brine, dried over anhyd MgSO$_4$, filtered and concentrated to give a thick clear oil, 4.66 g, 98.5%, R$_f$=0.23 on silica gel eluting with 5:1 hexanes:ethyl acetate. This material was used directly in the next step without further purification.

PART B

The product from Part A (4.66 g, 10.1 mmol) was dissolved in 40 mL of anhyd ethanol and treated with 30 mg of 15% palladium on carbon catalyst. This mixture was then hydrogenated for 18 h at room temperature and 40 psig. The catalyst was removed by filtration through diatomaceous earth and the filtrate concentrated to give an oil that was used directly in the next step without purification.

PART C

A mixture of 2(S)-methyl-3-methylsulfonyl propionic acid (1.39 g, 8.3 mmol), N-hydroxybenzotriazole (1.84 g, 12.0 mmol), and 1-(3-dimethylaminoproyl)-3-ethylcarbodiimide hydrochloride (EDC) (1.77 g, 9.2 mmol) was dissolved in 10 mL of dimethylformamide (DMF) and allowed to react for 30 min at 0° C. The amine from Part B (2.80 g, 8.0 mmol) dissolved in 10 mL of DMF was added to the above mixture and stirred at room temperature for 24 h. The solution was concentrated in vacuo and the residue taken up in ethyl acetate. The ethyl acetate solution was washed with 5% aqueous citric acid, saturated aqueous NaHCO$_3$, brine, dried over anhyd MgSO$_4$, filtered and concentrated to give a clear oil, that was purified by flash chromatography to give 3.00 g, 75%, this material was used directly in the next step.

PART D

The product from Part C (3.00 g, 6.02 mmol) was treated with 30 mL of 4N HCl in dioxane at room temperature for 24 h. The solution was concentrated in vacuo and the semi-solid residue was triturated with ether and dried under vacuum to give a white amorphous solid, mp>250° C., turns yellow at 221° C., FAB MS, MH$^+$=436.

PART E

The product from Part D was dissolved in dichloromethane and treated with saturated aqueous NaHCO$_3$ to provide a solution of the free amine. The organic phase was dried over anhyd MgSO$_4$, filtered and concentrated in vacuo to give (610 mg, 1.75 mmol). This amine was suspended in 50 mL of THF and treated sequentially with triethylamine (1.01 g, 10 mmol) and benzenesulfonyl chloride (283 mg, 1.75 mmol). The solution was stirred at room temperature for 19.5 h. The solids were removed by filtration and the filtrate concentrated and dissolved in dichloromethane. The dichloromethane solution was washed with 1N KHSO$_4$, saturated aqueous NaHCO$_3$, brine, dried over anhyd MgSO$_4$, filtered and concentrated to give an oil that was triturated with methanol to give a white solid that was isolated by filtration. The crude solid was then crystallized from ethyl acetate and hexanes to give 200 mg, 21% of material with mp 112°–115° C., HRFAB MS, calc'd. for $C_{26}H_{38}N_2O_6S_2$: 538.2171. Found: 533.2180.

EXAMPLE 5

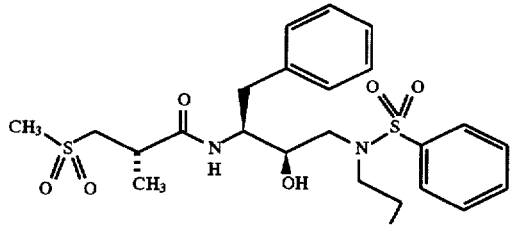

Preparation of propanamide, N-[2-hydroxy-3-(propyl) (phenylsulfonyl)amino]-1-(phenylmethyl) propyl]-2-methyl-3-(methylsulfonyl)-, [1S-[1R*(R*),2S*]]-

PART A

A solution of N-benzyloxycarbonyl 3(S)-amino-1,2-(S)-epoxy-4-phenylbutane (6.06 g, 20.4 mmol) and n-propylamine (20.9 g, 0.35 mmol) in 100 mL of isopropyl alcohol was heated to reflux for 3 h. The solution was then concentrated in vacuo to give a solid that was crystallized from hexanes and ethyl acetate to give 6.53 g, 90%, of the desired product, mp 120°–123° C., FAB MS: MH$^+$=357.

PART B

The amine from Part A was reacted with benzenesulfonyl chloride in a manner similar to Example 3, Part B. The resulting compound (1.426 g, 2.87 mmol) dissolved in 25 mL of methanol was hydrogenated over 40 mg of 10% palladium on carbon at 40 psig for 16 h at room temperature. The solution was then filtered through diatomaceous earth and the filtrate concentrated to give 1.04 g, 100%, of a clear oil that was used directly in the next step without further purification. HRFAB MS Calc'd for $C_{19}H_{24}N_2O_3S$: 363.1742. Found: 363.1763.

PART C

A mixture of 2(S)methyl-3 (methylsulfonyl)propionic acid (243.7 mg, 1.47 mmol), N-hydroxybenzotriazole (332.0 mg, 2.16 mmol), and EDC (304.8 mg, 1.59 mmol) in 2.5 mL of DMF was stirred at 0° C. for 0.5 h and then treated with a solution of the free amine from Part B (513.3 mg, 1.42 mmol) in 1.5 mL of DMF. The solution was stirred at room temperature for 16 h and then poured into 80 mL of 50% saturated aqueous $NaHCO_3$. The solution was extracted with ethyl acetate and the ethyl acetate solution was washed with 5% aqueous citric acid, saturated aqueous $NaHCO_3$, brine, dried over anhyd $MgSO_4$, filtered and concentrated to give-a white foam, 576.8 mg, that was purified by crystallized ethyl acetate/hexanes to give 441.1 mg, 61% of product with mp 134°–136.5° C.. HRFAB MS, Calc'd for $C_{24}H_{34}N_2O_6S_2$+ Li: 517.2019. Found: 517.1973.

EXAMPLE 6

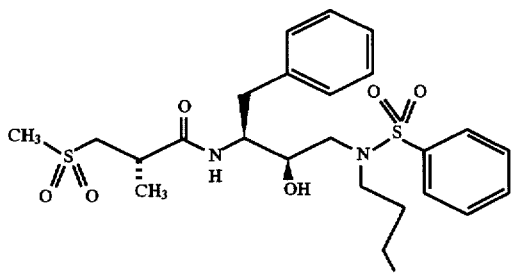

Preparation of propanamide, N-[2-hydroxy-3-(butyl) (phenylsulfonyl)amino]-1-(phenylmethyl) propyl]-2-methyl-3-(methylsulfonyl)-, [1S-[1R*(R*),2S*]]-

PART A

From the reaction of (1.48 g, 5.0 mmol) of N-benzyloxycarbonyl 3(S)-amino-1,2-(S)-epoxy-4-phenylbutane and (7.314 g, 100.0 mmol) of n-butylamine, one obtains 1.50 g (80%) of N-[3(S)-benzyloxycarbonylamino-2(R)-hydroxy-4-phenylbutyl]-N-butylamine, mp 125°–128° C., FAB MS, Spectrum: MH⁺= 371.

PART B

The amine from Part A (1.67 g, 4.5 mmol) and triethylamine (859.4 mg), was dissolved in 60 mL of dichloromethane and treated with benzene sulfonyl chloride (822.3 mg, 4.66 mmol) at room temperature. After stirring for 15 min. the solution was concentrated in vacuo and the residue dissolved in ethyl acetate. The ethyl acetate solution was washed with 1N $KHSO_4$, saturated aqueous $NaHCO_3$, brine, dried over anhyd $MgSO_4$, filtered and concentrated to give an oil. The oil was crystallized from hexanes and ether to give 2.04 g 89% of pure product, mp 68°–77° C.. FAB MS: MH⁺=511.

PART C

A solution of phenylmethyl [2(R)-hydroxy-3-[n-butyl] (benzenesulfonyl) amino]-1S-(phenylmethyl) propyl carbamate from Part B (1.86 g, 3.64 mmol) in 40 mL of methanol was hydrogenated over 110 mg of 10% palladium on carbon at 40 psig for 4 h. The solution was filtered through diatomaceous earth and concentrated in vacuo to give a solid, mp 68°–88° C., FAB MS: MH⁺=377, that was used in the next step without further purification.

PART D

A mixture of 2(S)methyl-3(methylsulfonyl)propionic acid (288.4 mg, 1.74 mmol), EDC (369.6 mg, 1.93 mmol), and N-hydroxybenzotriazole (368.1 mg, 2.41 mmol) was dissolved in 3.5 mL of DMF and stirred at 0° C. for 30 min. This solution was then treated with the amine from PART C (621.9 mg, 1.65 mmol) dissolved in 2 mL of DMF. The mixture was allowed to stir at room temperature for 48 h and then was concentrated in vacuo. The residue was dissolved in ethyl acetate, washed with 1N $KHSO_4$, saturated aqueous $NaHCO_3$, brine, dried over anhyd $MgSO_4$, filtered and concentrated in vacuo to give an oil. The crude product was purified by flash chromatography on silica get eluting with hexanes/ethyl acetate mixtures to give the desired product as a white solid, 353 mg, 41%, mp 99°–103° C., HRFAB MS: Calc'd for $C_{25}H_{36}N_2O_6S_2$: 531.2175. Found: 513.2176

EXAMPLE 7

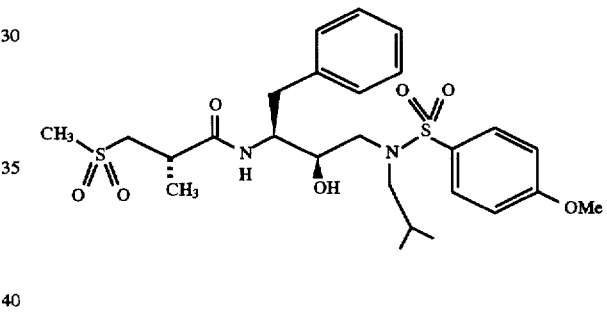

Preparation of propanamide, N-[2-hydroxy-3-[(2-methylpropyl) (4-methoxyphenylsulfonyl)amino]-1-(phenylmethyl)propyl]-2-methyl-3-(methylsulfonyl)-, [1S-[1R*(R*),2S*]]-

PART A

The amine from Example 3, Part A, N[3(S)-benzyloxycarbonylamino-2(R)-hydroxy-4-phenyl]N-isobutyl amine (1.1131 g, 3.00 mmol) and triethylamine (324.0 mg, 3.20 mmol) in 20 mL of dichloromethane was treated with 4-methoxy-benzenesulfonyl chloride (715.4 mg, 3.46 mmol). The solution was stirred at room temperature for 6 h and then was concentrated in vacuo. The residue was dissolved in ethyl acetate and washed with 1N $KHSO_4$, saturated aqueous $NaHCO_3$, brine, dried over anhyd $MgSO_4$, filtered, and concentrated to give a clear oil. The oil was crystallized from ether to give a white solid 1.273 g, 78%, mp 97°–101° C., of pure product, FAB MS; MH⁺=541.

PART B

The product from Part A (930 mg, 1.68 mmol) was dissolved in 30 mL of methanol and hydrogenated at 40 psig over 70 mg of 10% palladium on carbon at room temperature for 17 h. The catalyst was removed by filtration through diatomaceous earth and the filtrate was concentrated in vacuo to give 704 mg of a clear oil, that solidified upon standing, mp 105°–110° C., FAB MS, MH⁺=407, and was used directly in the next step without further purification.

PART C

A mixture of 2-methyl-3(methylsulfonyl)propionic acid (174.9 mg, 1.05 mmol), N-hydroxybenzotriazole (230 mg, 1.50 mmol) and EDC (220.5 mg, 1.15 mmol) in 2 mL of DMF was stirred at 0° C. for 0.5 mL and then treated with the amine from Part B (401.2 mg, 0.99 mmol) in 1 mL of DMF. The solution was stirred at room temperature for 16 h and then poured into 20 mL of saturated aqueous NaHCO$_3$. The aqueous solution was extracted with ethyl acetate and then the ethyl acetate solution was washed with 5% aqueous citric acid, saturated aqueous NaHCO$_3$, brine, dried over anhyd MgSO$_4$, filtered and concentrated in vacuo to give a clear oil, 260 mg, which was purified by flash chromatography on Silica gel eluting with hexanes and ethyl acetate to provide 52.7 mg, 9.6%, mp 87°–92° C., HRFAB MS; Calc'd for C$_{26}$H$_{38}$N$_2$O$_7$S$_2$: 555.2199. Found: 555.2234

EXAMPLE 8

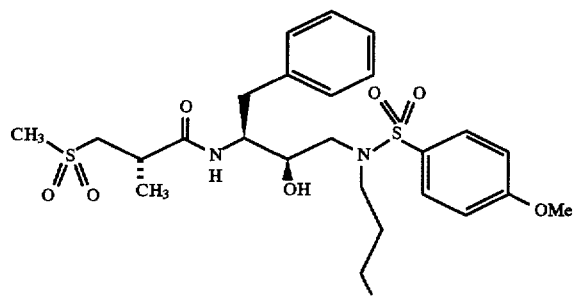

Preparation of propanamide, N-[2-hydroxy-3-[ (butyl) (4-methoxyphenylsulfonyl)amino]-1-(phenylmethyl)propyl]-2-methyl-3-(methylsulfonyl)-, [1S-[1R*(R*),2S*]]-

PART A

The amine from Example 6, Part A (1.52 mg, 4.10 mmol) and triethylamine (488 mg, 4.82 mmol) in 30 mL of dichloromethane was treated with 4-methoxybenzenesulfonyl chloride (869 mg, 4.20 mmol) at room temperature for 3 h. The solution was removed in vacuo and the residue was taken up in ethyl acetate. The ethyl acetate solution was washed with 1N KHSO$_4$, saturated aqueous NaHCO$_3$, brine, dried over anhyd MgSO$_4$, filtered and concentrated to give a white solid that was washed with ether and air dried to provide 1.71 g, 77%, mp 118°–120° C., FAB MS; M+Li= 547, of pure product.

PART B

The product from Part A (1.514 g, 2.80 mmol) in 30 mL of methanol was hydrogenated at 40 psig over 110 mg of 10% palladium on carbon for 16 h at room temperature. The catalyst was removed by filtration through diatomaceous earth and the filtrate concentrated to give a white solid, 1.20 g, 100%, mp 103°–108° C., HRFAB MS; Calc'd for C$_{21}$H$_{30}$N$_2$O$_4$S: 413.2086. Found: 413.2121, which was used directly in the next step without further purification.

PART C

A mixture of 2(S)-methyl-3(methylsulfonyl)propionic acid (354.4 mg, 2.13 mmol), N-hydroxybenzotriazole (473.4 mg, 3.09 mmol) and EDC (445.3 mg, 2.33 mmol) in 1.5 mL of DMF was stirred at 0° C. for 25 min. and then treated with the amine from Part B (815 mg, 2.00 mmol) in 2 mL of DMF. The mixture was stirred at room temperature for 16 h and then poured into 50 mL of saturated aqueous NaHCO$_3$ and then extracted with ethyl acetate. The ethyl acetate solution was washed with 5% aqueous citric acid, saturated aqueous NaHCO$_3$, brine, dried over anhyd MgSO$_4$, filtered and concentrated in vacuo to give 905 mg of a white foam. The product was purified by flash chromatography on Silica gel eluting with ethyl acetate/hexanes to provide 711.6 mg, 65%, of pure product, mp 87°–92° C., HRFAB MS, M+Li; Calc'd for C$_{26}$H$_{38}$N$_2$O$_7$S$_2$Li: 561.2281 Found: 561.2346

EXAMPLE 9

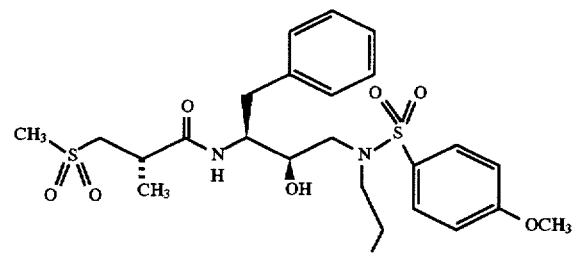

Preparation of propanamide, N-[2-hydroxy-3-[ (propyl) (4-methoxyphenylsulfonyl)amino]-1-(phenylmethyl)propyl]-2-methyl-3-(methylsulfonyl)-, [1S-[1R*(R*),2S*]]-

PART A

A solution of the product from Example 5, Part A (620 mg, 1.74 mmol) and triethylamine (250 mg, 2.47 mmol) in 15 mL of dichloromethane was treated with 4-methoxybenzenesulfonyl chloride (371 mg, 1.79 mmol) at room temperature for 2.33 h. The solvent was removed in vacuo and the residue taken up in ethyl acetate and then washed with 1N KHSO$_4$, saturated aqueous NaHCO$_3$, brine, dried over anhyd MgSO$_4$, filtered and concentrated to give 1.0622 g, of a white foam. The crude product was purified by flash chromatography over silica gel eluting with hexanes and ethyl acetate to give 615 mg, 67%, of pure product with mp 88°–92° C., HRFAB MS; calc'd. for C$_{28}$H$_{34}$N$_2$O$_6$S: 533.2298. Found: 533.2329.

PART B

A solution of carbamic acid, product from Part A (519 mg, 0.98 mmol) in 30 mL of methanol was treated with 70 mg of 10% palladium on carbon catalyst and hydrogenated at 46 psig for 22 h at room temperature. The catalyst was removed by filtration through diatomaceous earth and the filtrate concentrated in vacuo to give a clear oil that solidified upon standing, mp 124°–127° C., FAB MS; M+Li$^+$=399, 387 mg, 100%, that was used directly in the next step.

PART C

A mixture of 2(S)-methyl-3-methylsulfonyl propionic acid (138.5 mg, 0.83 mmol), N-hydroxybenzotriazole (174.6 mg, 1.14 mmol), and 1-(3-dimethylaminopropyl)-3-ethylcarbodiimide hydrochloride (EDC) (171.8 mg, 0.90 mmol) was dissolved in 2.5 mL of dimethylformamide (DMF) and allowed to react for 30 min at 0° C. The amine from Part B (304.9 mg, 0.78 mmol) dissolved in 1.5 mL of DMF was added to the above mixture and stirred at room temperature for 14.5 h. The solution was then poured into 20 mL of saturated aqueous NaHCO$_3$ and extracted with ethyl acetate. The ethyl acetate extracts were washed with 5% aqueous citric acid, saturated aqueous NaHCO$_3$, brine, dried over anhyd MgSO$_4$, filtered and concentrated to give a white solid. The material was recrystallized from hexanes and ethyl acetate to give 228 mg, 54% of pure product with mp 115°–118° C. HRFAB MS; calc'd. for C$_{27}$H$_{40}$N$_2$O$_7$S2: 541.2042. Found: 541.2064.

EXAMPLE 10

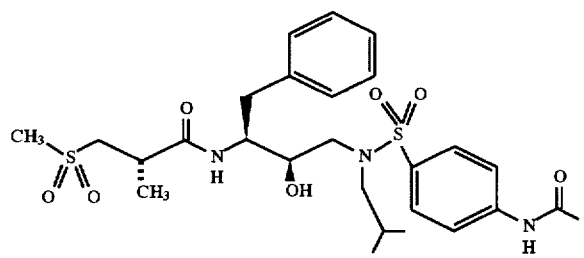

Preparation of propanamide, N-[2-hydroxy-3-[(2-methylpropyl)(4-acetamido)phenylsulfonyl)amino]-1-(phenylmethyl)propyl]-2-methyl-3-methylsulfonyl)-, [1S-[1R*(R*),2S*]]-

PART A

A solution of the product from Example 3, Part A (1.1082 g, 2.99 mmol) and triethylamine (713 mg, 3.05 mmol) in 20 mL of dichloromethane was treated with N-acetylsulfanilyl chloride (713.2 mg, 3.05 mmol) at room temperature for 3.67 h. The solvent was removed in vacuo and the residue taken up in ethyl acetate and then washed with 1N $KHSO_4$, saturated aqueous $NaHCO_3$, brine, dried over anhyd $MgSO_4$, filtered and concentrated to give 1.398 g, of a white solid, mp 155°–158° C., FAB MS; M+Li=574.

PART B

A solution of product from Part A (900 mg, 1.58 mmol) in 30 mL of methanol was treated with 90 mg of 10% palladium on carbon catalyst and hydrogenated at 32 psig for 15 h at room temperature. The catalyst was removed by filtration through diatomaceous earth and the filtrate concentrated in vacuo to give a white foam, FAB MS; M+H$^+$ =334, 680 mg, 99%, that was used directly in the next step without further purification.

PART C

A mixture of 2(S)-methyl-3-methylsulfonyl propionic acid (159.7 mg, 0.96 mmol), N-hydroxybenzotriazole (210.8 mg, 1.38 mmol), and 1-(3-dimethylaminopropyl)-3-ethylcarbodiimide hydrochloride (EDC) (203.9 mg, 1.06 mmol) was dissolved in 1.5 mL of dimethylformamide (DMF) and allowed to react for 30 min at 0° C. The amine from Part B (401.9 mg, 1.06 mmol) dissolved in 0.5 mL of DMF was added to the Above mixture and stirred at room temperature for 16.5 h. The solution was then poured into 75 mL of saturated aqueous $NaHCO_3$ and extracted with ethyl acetate. The ethyl acetate extracts were washed with 5% aqueous citric acid, saturated aqueous $NaHCO_3$, brine, dried over anhyd $MgSO_4$, filtered and concentrated to give a white foam, 490 mg. The material was crystallized from hexanes and ethyl acetate to give 428 mg, 80% of pure product with mp 123°–127° C. HRFAB MS; calc'd. for $C_{27}H_{39}N_3O_7S_2$: 588.2398. Found: 588.2395.

EXAMPLE 11

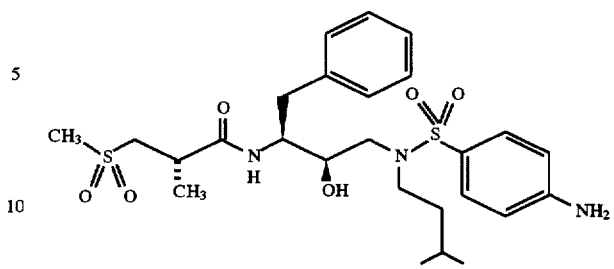

Preparation of propanamide, N-[2-hydroxy-3-[(3-methylbutyl)(4-aminophenylsulfonyl)amino]-1-(phenylmethyl)propyl]-2-methyl-3-(methylsulfonyl)-, [1S-[1R*(R*), 2S*]]-

PART A

A solution of product from Example 1, Part C (1.1812 g, 3.07 mmol) and triethylamine (325.7 mg, 3.22 mmol) in 20 mL of dichloromethane was treated with 4-nitrobenzensulfonyl chloride (767 mg, 90% purity 3.11 mmol) at room temperature for 10 min. The solvent was removed in vacuo and the residue taken up in ethyl acetate and then washed with 1N $KHSO_4$, saturated aqueous $NaHCO_3$, brine, dried over anhyd $MgSO_4$, filtered and concentrated to give 2.3230 g, of a tan solid, that was crystallized from ethyl acetate and petroleum ether to provide 870 mg, 50% mp 130°–132° C. of pure product, HRFAB MS; M+Li, calc'd. for $C_{29}H_{35}N_3O_7SLi$: 576.2316. Found: 576.2350.

PART B

A solution of product from Part A (574 mg, 1.01 mmol) in 40 mL of methanol, (the solution was not completely homogeneous), was treated with 70 mg of 10% palladium on carbon catalyst and hydrogenated at 42 psig for 15 h at room temperature. The catalyst was removed by filtration through diatomaceous earth and the filtrate concentrated in vacuo to give a white solid that was crystallized from chloroform, mp 123°–127° C., FAB MS; M+Li$^+$=412, 400 mg, 91%, that was used directly in the next step without further purification.

PART C

A mixture of 2(S)-methyl-3-methylsulfonyl propionic acid (112.3 mg, 0.675 mmol), N-hydroxybenzotriazole (159.1 mg, 1.04 mmol), and 1-(3-dimethylaminopropyl)-3-ethylcarbodiimide hydrochloride (EDC) (147.8 mg, 0.77 mmol) was dissolved in 1.0 mL of dimethylformamide (DMF) and allowed to react for 30 min at 0° C. The amine from Part B (261.9 mg, 0.646 mmol) dissolved in 0.5 mL of DMF was added to the above mixture and stirred at room temperature for 16.5 h. The solution was then poured into 75 mL of saturated aqueous $NaHCO_3$ and extracted with ethyl acetate. The ethyl acetate extracts were washed with 5% aqueous citric acid, saturated aqueous $NaHCO_3$, brine, dried over anhyd $MgSO_4$, filtered and concentrated to give a white foam, 326.3 mg. The material was purified by flash chromatography over silica gel eluting with ethyl acetate to provide 213.6 mg, 64% of pure product as a white foam, FAB MS; MH$^+$=554.

EXAMPLE 12

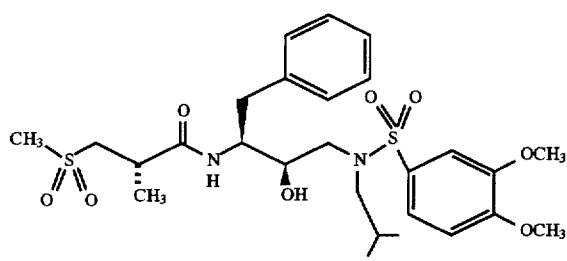

Preparation of Propanamide, N-[2-hydroxy-3-[(2-methylpropyl)(3,4-dimethoxyphenylsulfonyl)amino]-1-(phenylmethyl)propyl]-2-methyl-3-(methylsulfonyl)-, [1S-[1R*(R*),2S*]]-

PART A

A solution of the product from Example 3, Part A (1.5356 g, 4.14 mmol) and triethylamine (522 mg, 5.17 mmol) in 15 mL of dichloromethane was treated with 3,4-dimethoxybenzenesulfonyl chloride (1.0087 g, 4.26 mmol) at room temperature for 14 h. The solvent was removed in vacuo and the residue taken up in ethyl acetate and then washed with 1N $KHSO_4$, saturated aqueous $NaHCO_3$, brine, dried over anhyd $MgSO_4$, filtered and concentrated to give 2.147 g, 90.5%, of a white solid, mp 124°–127° C., HRFAB MS; M+Li; calc'd. for $C_{30}H_{38}N_2O_7S$+Li: 577.2560. Found: 577.2604.

PART B

A solution of carbamic acid, product from Part A (513 mg, 0.90 mmol) in 30 mL of methanol was stirred with 20 mg of palladium black catalyst and 10 mL of formic acid for 15 h at room temperature. The catalyst was removed by filtration through diatomaceous earth and the filtrate concentrated in vacuo and the residue taken up in ethyl acetate. The ethyl acetate solution was washed with saturated aqueous $NaHCO_3$, brine and dried over anhyd $MgSO_4$, filtered and concentrated in vacuo to give a white solid, 386 mg, 98%, mp 123°–130° C., FAB MS; M+Li$^+$=443, that was used directly in the next step without further purification.

PART C

A mixture of 2(S)-methyl-3-methylsulfonyl propionic acid (128 mg, 0.77 mmol), N-hydroxybenzotriazole (179.9 mg, 1.17 mmol), and 1-(3-dimethylaminopropyl)-3-ethylcarbodiimide hydrochloride (EDC) (177.3 mg, 0.92 mmol) was dissolved in 1.5 mL of dimethylformamide (DMF) and allowed to react for 30 min at 0° C. The amine from Part B (359 mg, 0.82 mmol) dissolved in 1 mL of DMF was added to the above mixture and stirred at room temperature for 48 h. The solution was then poured into 75 mL of saturated aqueous $NaHCO_3$ and extracted with ethyl acetate. The ethyl acetate extracts were washed with 5% aqueous citric acid, saturated aqueous $NaHCO_3$, brine, dried over anhyd $MgSO_4$, filtered and concentrated to give a clear oil, 220 mg. The material was crystallized from hexanes and ethyl acetate to give 178 mg, 40% of pure product with mp 130°–133° C. HRFAB MS;M+Li$^+$; calc'd. for $C_{27}H_{40}N_2O_8S_2$Li: 591.2386. Found: 591.2396.

EXAMPLE 13

Preparation of Propanamide, N-[2-hydroxy-3-[(2-methylpropyl)(4-hydroxyphenylsulfonyl)amino]-1-(phenylmethyl)propyl]-2-methyl-3-(methylsulfonyl)-, [1S-[1R*(R*), 2S*]]-

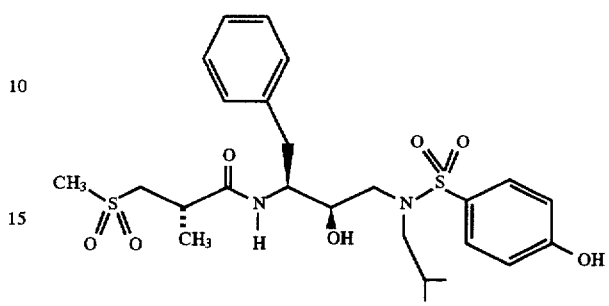

Part A: A solution of 0.98 g (1.85 mmol) of carbamic acid, [2R-hydroxy-3-[[(4-fluorophenyl)sulfonyl](2-methylpropyl)amino]-1S-(phenylmethyl)propyl]-phenylmethyl ester in 3.8 mL of anhydrous DMF was added to 22 mg (7.4 mmol) of 80% sodium hydride in 2 mL of DMF. To this mixture was added 0.40 g (3.7 mmol) of benzyl alcohol. After 2 hours, the solution was cooled to 0 C, water added, and then ethyl acetate. The organic layer was washed with 5% citric acid, saturated sodium bicarbonate and brine, dried over magnesium sulfate, filtered and concentrated to afford 0.90 g of crude material. This was chromatographed on basic alumina using 3% methanol/methylene chloride to afford 0.70 g of 2R-hydroxy-3-[(2-methylpropyl)(4-benzyloxyphenyl)sulfonyl]amino-1S-(phenylmethyl)propylamine, cyclic carbamate; mass spectrum m/e=509(M+H).

Part B: To a solution of 0.65g (1.28 mmol) of the cyclic carbamate from part A in 15 mL of ethanol, was added 2.6 mL (6.4 mmol) of 25N sodium hydroxide solution. After 1 hour at reflux, 4 mL of water was added and the solution refluxed for an additional eight hours. The volatiles were removed, ethyl acetate added, and washed with water, brine, dried over magnesium sulfate, filtered and concentrated to afford 550 mg of crude 2R-hydroxy-3-[(2-methylpropyl)(4-benzyloxyphenyl) sulfonyl]amino-1S-(phenylmethyl) propylamine.

Part C: A solution of crude 2R-hydroxy-3-[(2-methylpropyl) (4-benzyloxyphenyl)sulfonyl] amino-1S-(phenylmethyl)propylamine in 10 mL of ethanol was hydrogenated in the presence of 500 mg of a 10% palladium on carbon catalyst under 50 psig of hydrogen for 2 hours. The catalyst was removed by filtration and the solvent removed in vacuo to afford 330 mg of 2R-hydroxy-3-[(2-methylpropyl) (4- hydroxyphenyl)sulfonyl]amino-1S-(phenylmethyl)propylamine, mass spectrum m/e=393 (M+H).

Part D: To a solution of 337 mg (2.03 mmol) of 2(S)-methyl-3-(methylsulfonyl)propionic acid and 423 mg (2.21 mmol) of N-hydroxybenzotriazole in 4 mL of anhydrous DMF at 0 C., was added 423 mg (2.76 mmol) of 1-(3-dimethylaminopropyl)-3-ethylcarbodiimide hydrochloride. After stirring for 2 hours, 725 mg (1.84 mmol) of amine from part C above was added and the solution stirred at room temperature for 17 hours. The solvent was removed in vacuo, ethyl acetate added, and then washed with saturated aqueous sodium bicarbonate, brine, dried over magnesium sulfate, filtered and concentrated to afford 939 mg of crude product. Chromatography on silica gel using 2–5% methanol/methylene chloride afforded 533 mg of propanamide, N-[2-hydroxy-3-[(2-methylpropyl)(4-hydroxyphenylsulfonyl)amino]-1-(phenylmethyl)propyl]-2-methyl-3-(methylsulfonyl)-, [1S-[1R*(R*), 2S*]]-, mass spectrum m/e=547 (M+Li).

EXAMPLE 14

The following general procedures can be utilized to prepare additional compounds within the scope of the present invention.

General Procedure for the Synthesis of Amino Epoxides

To a solution of 0.226 mol of N-benzyloxycarbonyl-L-phenylalanine chloromethyl ketone in a mixture of 807 mL of methanol and 807 mL of tetrahydrofuran at $-2°$ C., is added 1.54 equiv. of solid sodium borohydride over one hundred minutes. The solvents are then removed under reduced pressure at $40°$ C. and the residue is dissolved in ethyl acetate (approx. 1 L). The solution is washed sequentially with 1M potassium hydrogen sulfate, saturated sodium bicarbonate and is then saturated sodium chloride solutions. After drying over anhydrous magnesium sulfate and filtering, the solution is removed under reduced pressure. To the resulting oil is added hexane (approx. 1 L) and the mixture is warmed to $60°$ C. with swirling. After cooling to room temperature, the solids are collected and washed with 2 L of hexane. The resulting solid is recrystallized from hot ethyl acetate and hexane to afford 32.3 g (43% yield) of N-benzyloxycarbonyl-3(S)-amino-1-chloro-4-phenyl-2(S)-butanol, mp $150°–151°$ C. and $M+Li^+=340$.

PART B:

To a solution of 1.2 equiv. of potassium hydroxide in 968 mL of absolute ethanol at room temperature, is added 0.097 mol of N-CBZ-3(S)-amino-1-chloro-4-phenyl-2(S)-butanol. After stirring for fifteen minutes, the solvent is removed under reduced pressure and the solids are dissolved in methylene chloride. After washing with water, drying over magnesium sulfate, filtering and stripping, one obtains a white solid. Recrystallization from hot ethyl acetate and hexane will afford N-benzyloxycarbonyl-3(S)-amino-1,2(S)-epoxy-4-phenylbutane.

Alternate Procedure for the Synthesis of Amino Epoxides

Step A

A solution of L-phenylalanine (50.0 g, 0.302 mol), sodium hydroxide (24.2 g, 0.605 mol) and potassium carbonate (83.6 g, 0.605 mol) in water (500 ml) is heated to $97°$ C. Benzyl bromide (108.5 ml, 0.912 mol) is then slowly added (addition time ~25 min). The mixture is then stirred at $97°$ C. for 30 minutes. The solution is cooled to room temperature and extracted with toluene (2×250 ml). The combined organic layers are then washed with water, brine, dried over magnesium sulfate, filtered and concentrated to give an oil product. The crude product is then used in the next step without purification.

Step B

The crude benzylated product of the above step is dissolved in toluene (750 ml) and cooled to $-55°$ C. A 1.5M solution of DIBAL-H in toluene (443.9 ml, 0.666 mol) is then added at a rate to maintain the temperature between $-55°$ to $-50°$ C. (addition time ~1 hour). The mixture is stirred for 20 minutes at $-55°$ C. The reaction is quenched at $-55°$ C. by the slow addition of methanol (37 ml). The cold solution is then poured into cold ($5°$ C.) 1.5N HCl solution (1.8 L). The precipitated solid (approx. 138 g) is filtered off and washed with toluene. The solid material is suspended in a mixture of toluene (400 ml) and water (100 ml). The mixture is cooled to $5°$ C., treated with 2.5N NaOH (186 ml) and then stirred at room temperature until the solid is dissolved. The toluene layer is separated from the aqueous phase and washed with water and brine, dried over magnesium sulfate, filtered and concentrated to a volume of 75 ml (89 g). Ethyl acetate (25 ml) and hexane (25 ml) are then added to the residue upon which the alcohol product begins to crystallize. After 30 min., an additional 50 ml hexane is added to promote further crystallization. The solid is filtered off and washed with 50 ml hexane to give approximately 35 g of material. A second crop of material can be isolated by refiltering the mother liquor. The solids are combined and recrystallized from ethyl acetate (20 ml) and hexane (30 ml) to give, in 2 crops, approximately 40 g (40% from L-phenylalanine) of analytically pure alcohol product. The mother liquors are combined and concentrated (34 g). The residue is treated with ethyl acetate and hexane which provides an additional 7 g (~7% yield) of slightly impure solid product. Further optimization in the recovery from the mother liquor is probable.

Step C

A solution of oxalyl chloride (8.4 ml, 0.096 mol) in dichloromethane (240 ml) is cooled to $-74°$ C. A solution of DMSO (12.0 ml, 0.155 mol) in dichloromethane (50 ml) is then slowly added at a rate to maintain the temperature at $-74°$ C. (addition time ~1.25 hr). The mixture is stirred for 5 min. followed by addition of a solution of the alcohol (0.074 mol) in 100 ml of dichloromethane (addition time –20 min., temp. $-75°$ C. to $-68°$ C.). The solution is stirred at $-78°$ C. for 35 minutes. Triethylamine (41.2 ml, 0.295 mol) is then added over 10 min. (temp. $-78°$ to $-68°$ C.) upon which the ammonium salt precipitated. The cold mixture is stirred for 30 min. and then water (225 ml) is added. The dichloromethane layer is separated from the aqueous phase and washed with water, brine, dried over magnesium sulfate, filtered and concentrated. The residue is diluted with ethyl acetate and hexane and then filtered to further remove the ammonium salt. The filtrate is concentrated to give the desired aldehyde product. The aldehyde was carried on to the next step without purification.

Temperatures higher than $-70°$ C. have been reported in the literature for the Swern oxidation. Other Swern modifications and alternatives to the Swern oxidations are also possible.

A solution of the crude aldehyde 0.074 mol and chloroiodomethane (7.0 ml, 0.096 mol) in tetrahydrofuran (285 ml) is cooled to $-78°$ C. A 1.6M solution of n-butyllithium in hexane (25 ml, 0.040 mol) is then added at a rate to maintain the temperature at $-75°$ C. (addition time –15 min.). After the first addition, additional chloroiodomethane (1.6 ml, 0.022 mol) is added again, followed by n-butyllithium (23 ml, 0.037 mol), keeping the temperature at $-75°$ C. The mixture is stirred for 15 min. Each of the reagents, chloroiodomethane (0.70 ml, 0.010 mol) and n-butyllithium (5 ml, 0.008 mol) are added 4 more times over 45 min. at $-75°$ C. The cooling bath is then removed and the solution warmed to $22°$ C. over 1.5 hr. The mixture is poured into 300 ml of saturated aq. ammonium chloride solution. The tetrahydrofuran layer is separated. The aqueous phase is extracted with ethyl acetate (1×300 ml). The combined organic layers are washed with brine, dried over magnesium sulfate, filtered and concentrated to give a brown oil (27.4 g). The product could be used in the next step without purification. The desired diastereomer can be purified by recrystallization at the subsequent sulfonamide formation step. Alternately, the product could be purified by chromatography.

General Procedure for the Synthesis of 1,3-Diamino 4-phenyl Butan-2-ol Derivatives (Amino Alcohols)

A mixture of the amine $R^3NH_2$ (20 equiv.) in dry isopropyl alcohol (20 mL/mmol of epoxide to be converted) is heated to reflux and then is treated with an N-Cbz amino epoxide of the formula:

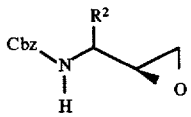

from a solids addition funnel over a 10–15 minute period. After the addition is complete the solution is maintained at reflux for an additional 15 minutes and the progress of the reaction monitored by TLC. The reaction mixture is then concentrated in vacuo to give an oil and is then treated with n-hexane with rapid stirring whereupon the ring opened-material precipitates from solution. Precipitation is generally complete within 1 hr and the product is then isolated by filtration on a Büchner funnel and is then air dried. The product is further dried in vacuo. This method affords amino alcohols of sufficient purity for most purposes.

Table 1 shows representative amino alcohols prepared according to the above general procedures.

TABLE 1

| Entry | $R^3$ |
|---|---|
| 1 | i-Butyl |
| 2 | $CH_3$ |
| 3 | i-Propyl |
| 4 | $-CH_2CH(CH_3)_2$ |
| 5 | i-Propyl |
| 6 | Phenyl |
| 7 | Benzyl |
| 8 | Oyclohexylmethyl |
| 9 | Cyclohexyl |
| 10 | 2-Naphthylmethyl |
| 11 | n-Butyl |
| 12 | n-Pentyl |
| 13 | n-Hexyl |
| 14 | p-Methyoxybenzyl |
| 15 | 3-Pyridylmethyl |
| 16 | 4-Pyridylmethyl |
| 17 | n-Butoxy |
| 18 | p-Fluorobenzyl |

General procedure for the Reaction of Amino Alcohols with Sulfonyl Halides or Sulfonyl Anhydrides: Preparation of Sulfonamides To a solution of N[3(S)-benzyloxycarbonylamino-2(R)-hydroxy-4-phenylbutyl] N-isoamylamine (2.0 gm, 5.2 mmol) and triethylamine (723 uL, 5.5 mmol) in dichloromethane (20 mL) is added dropwise methanesulfonyl chloride (400 uL, 5.2 mmol). The reaction mixture is stirred for 2 hours at room temperature, then the dichloromethane solution is concentrated to ca. 5 mL and applied to a silica gel column (100 gm). The column is eluted with chloroform containing 1% ethanol and 1% methanol.

Alternatively, from the reaction of N[3(S)-benzyloxycarbonylamino-2(R)-hydroxy-4-phenylbutyl] N-isoamylamine (1.47 gm, 3.8 mmol), triethylamine (528 uL, 3.8 mmol) and benzenesulfonyl chloride (483 uL, 3.8 mmol) one can obtain the appropriate (phenylsulfonyl) amino derivative.

The following Table 2 shows representative sulfonamides prepared according to the above procedure.

TABLE 2

| Entry | $R^3$ | $R^4$ |
|---|---|---|
| 1 | isoamyl | p-fluorophenyl |
| 2 | isoamyl | p-nitrophenyl |
| 3 | isoamyl | o-nitrophenyl |
| 4 | isoamyl | β-naphthyl |
| 5 | isoamyl | 2-thienyl |
| 6 | isoamyl | benzyl |
| 7 | isobutyl | p-fluorophenyl |
| 8 | p-fluorobenzyl | phenyl |
| 9 | 4-methylpyridyl | phenyl |
| 10 | cyclohexylmethyl | phenyl |
| 11 | allyl | phenyl |
| 12 | propyl | phenyl |
| 13 | cyclopropylmethyl | phenyl |
| 14 | methyl | phenyl |
| 15 | propargyl | phenyl |
| 16 | isoamyl | p-chlorophenyl |
| 17 | isoamyl | p-methoxyphenyl |
| 18 | isoamyl | m-nitrophenyl |
| 19 | isoamyl | m-trifluoromethylphenyl |
| 20 | isoamyl | o-methoxycarbonylphenyl |
| 21 | isoamyl | p-acetamidophenyl |
| 22 | isobutyl | phenyl |
| 23 | $-CH_2Ph$ | $-Ph$ |
| 24 | $-CH_2$-C$_6$H$_4$-F | $-Ph$ |
| 25 | $-CH_2$-cyclohexyl | $-Ph$ |
| 26 | $-CH_2$-C$_6$H$_4$-$OCH_3$ | $-Ph$ |
| 27 | $-CH_2$-pyridyl | $-Ph$ |
| 28 | $-CH_2$-cyclopropyl | $-Ph$ |
| 29 | $-CH_2CH=CH_2$ | $-Ph$ |
| 30 | phenyl | $-Ph$ |
| 31 | cyclohexyl | $-Ph$ |
| 32 | $-CH_2CH_2Ph$ | $-Ph$ |

TABLE 2-continued

Cbz—NH—CH(CH₂Ph)—CH(OH)—CH₂—N(R³)—S(O)₂—R⁴

| Entry | R³ | R⁴ |
|---|---|---|
| 33 | —CH₂CH₂CH₂CH₂OH | —Ph |
| 34 | —CH₂CH₂N(CH₃)₂ | —Ph |
| 35 | —CH₂CH₂—N(morpholine) | —Ph |
| 36 | —CH₃ | —Ph |
| 37 | —CH₂CH₂CH₂SCH₃ | —Ph |
| 38 | —CH₂CH₂CH₂S(O)₂CH₃ | —Ph |
| 39 | —CH₂CH₂CH(CH₃)₂ | —Ph |
| 40 | —CH₂CH₂CH(CH₃)₂ | —CH₂CH₂CH₃ |
| 41 | —CH₂CH₂CH(CH₃)₂ | —CH₃ |
| 42 | —CH₂CH₂CH(CH₃)₂ | —C₆H₄-F |
| 43 | —CH₂CH₂CH(CH₃)₂ | —C₆H₄-CH₃ |
| 44 | —CH₂CH₂CH(CH₃)₂ | —C₆H₄-CO₂CH₃ |
| 45 | —CH₂CH(CH₃)₂ | —C₆H₄-F |
| 46 | —CH₂CH(CH₃)₂ | —C₆H₄-NHAc |
| 47 | —CH₂CH(CH₃)₂ | —C₆H₄-CH₃ |
| 48 | —CH₂CH₂CH₃ | —C₆H₄-OCH₃ |
| 49 | —CH₂CH₂CH₂CH₃ | —C₆H₄-OCH₃ |

General Procedure for the Removal of the Protecting Groups by Hydrogenolysis with Palladium on Carbon A. Alcohol Solvent The Cbz-protected peptide derivative is dissolved in methanol (ca.20 mL/mmol) and 10% palladium on carbon catalyst is added under a nitrogen atmosphere. The reaction vessel is sealed and flushed 5 times with nitrogen and then 5 times with hydrogen. The pressure is maintained at 50 psig for 1–16 hours and then the hydrogen is replaced with nitrogen and the solution is filtered through a pad of celite to remove the catalyst. The solvent is removed in vacuo to give the free amino derivative of suitable purity to be taken directly on to the next step.

B. Acetic Acid Solvent

The Cbz-protected peptide derivative is dissolved in glacial acetic acid (20 mL/mmol) and 10% palladium on carbon catalyst is added under a nitrogen atmosphere. The reaction vessel is flushed 5 times with nitrogen and 5 times with hydrogen and then maintained at 40 psig for about 2 h. The hydrogen is then replaced with nitrogen and the reaction mixture filtered through a pad of celite to remove the catalyst. The filtrate is concentrated and the resulting product is taken up in anhydrous ether and is evaporated to dryness 3 times. The final product, the acetate salt, is dried in vacuo and is of suitable purity for subsequent conversion.

General Procedure for Removal of Boc-protecting Group with 4N Hydrochloric Acid in Dioxane The Boc-protected amino acid or peptide derivative is treated with a solution of 4N HCl in dioxane with stirring at room temperature. Generally the deprotection reaction is complete within 15 minutes, the progress of the reaction is monitored by thin layer chromatography (TLC). Upon completion, the excess dioxane and HCl are removed by evaporation in vacuo. The last traces of dioxane and HCl are best removed by evaporation again from anhydrous ether or acetone. The hydrochloride salt thus obtained is thoroughly dried in vacuo and is suitable for further reaction.

Procedures for Preparation of Sulfonyl Compounds

The procedures described below in Examples 13A, 13B and 13C illustrate procedures for preparing sulfonyl alkanoyl compounds which can be coupled to the sulfonamides as prepared above.

EXAMPLE 14A

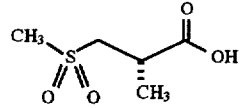

Preparation of 2(S)-methyl-3-(methylsulfonyl)propionic Acid

To a solution of 10 g of D-(−)-S-benzoyl-b-mercaptoisobutyric acid t-butyl ester in 20 mL of methanol was bubbled in gaseous ammonia at 0° C. The reaction was allowed to then warm to room temperature, stirred overnight and concentrated under reduced pressure. The resulting mixture of a solid (benzamide) and liquid was filtered to provide 5.21 g of a pale oil which then solidified. This was identified as 2(S)-methyl-3-mercaptopropionic acid t-butyl ester.

To a solution of 5.21 g of 2(S)-methyl-3-mercaptopropionic acid t-butyl ester in 75 mL of toluene at 0° C. was added 4.50 g of 1.8-diazabicyclo|5.40|undec-7-ene and 1.94 mL of methyl iodide. After stirring at room temperature for 2.5 hours, the volatiles were removed, ethyl acetate added, washed with dilute hydrochloric acid, water, brine, dried and concentrated to afford 2.82 g of a pale oil, identified as 2(S)-methyl-3-(thiomethyl)propionic acid t-butyl ester.

To a solution of 2.82 g of 2(S)-methyl-3-(thiomethyl) propionic acid t-butyl ester in 50 mL of acetic acid was added 5.58 g of sodium perborate and the mixture heated to 55° C. for 17 hours. The reaction was poured into water, extracted with methylene chloride, washed with aqueous sodium bicarbonate, dried and concentrated to afford 2.68 g of 2(S)-methyl-3-(methylsulfonyl)propionic acid t-butyl ester as a white solid.

To 2.68 g of 2(S)-methyl-3-(methylsulfonyl)-propionic acid t-butyl ester was added 20 mL of 4N hydrochloric acid/dioxane and the mixture stirred at room temperature for 19 hours. The solvent was removed under reduced pressure to afford 2.18 g of crude product, which was recrystallized from ethyl acetate/hexane to yield 1.44 g of 2(S)-methyl-3-(methylsulfonyl)propionic acid as white crystals.

EXAMPLE 14B
PART A

A solution of methyl methacrylate (7.25 g, 72.5 mmol) and phenethyl mercaptan (10.0 g, 72.5 mmol) in 100 mL of methanol was cooled in an ice bath and treated with sodium methoxide (100 mg, 1.85 mmol). The solution was stirred under nitrogen for 3 h and then concentrated in vacuo to give an oil that was taken up in ether and washed with 1N aqueous potassium hydrogen sulfate, saturated aqueous sodium chloride, dried over anhydrous magnesium sulfate, filtered and concentrated to give 16.83 g, 97.5% of methyl 2-(R,S)-methyl-4-thia-6-phenyl hexanoate as an oil. TLC on $SiO_2$ eluting with 20:1 hexane:ethyl acetate (v:v) $R_f$=0.41. Alternatively, one can use methyl 3-bromo-2-methyl propionate in place of methyl methacrylate.

PART B

A solution of methyl 2-(R,S)-methyl-4-thia-6-phenyl hexanoate (4.00 g, 16.8 mmol) in 100 mL of dichloromethane was stirred at room temperature and treated portion wise with meta-chloroperoxybenzoic acid (7.38 g, 39.2 mmol) over approximately 40 m. The solution was stirred at room temperature for 16 h and then filtered and the filtrate washed with saturated aqueous sodium bicarbonate, 1N sodium hydroxide, saturated aqueous sodium chloride, dried over anhydrous magnesium sulfate, filtered, and concentrated to give 4.50 g, 99% of desired sulfone. The unpurified sulfone was dissolved in 100 mL of tetrahydrofuran and treated with a solution of lithium hydroxide (1.04 g, 24.5 mmol) in 40 mL of water. The solution was stirred at room temperature for 2 m and then concentrated in vacuo. The residue was then acidified with 1N aqueous potassium hydrogen sulfate to pH=1 and then extracted three times with ethyl acetate. The combined ethyl acetate solution was washed with saturated aqueous sodium chloride, dried over anhydrous magnesium sulfate, filtered and concentrated to give a white solid. The solid was taken up in boiling ethyl acetate/hexane and allowed to stand undisturbed whereupon white needles formed that were isolated by filtration and air dried to give 3.38 g, 79% of 2-(R,S)-methyl-3(β-phenethylsulfonyl)-propionic acid, mp 91°–93° C.

PART C

A solution of 2-(R,S)-methyl-3(β-phenethylsulfonyl)-propionic acid (166.1 mg, 0.65 mmol), N-hydroxybenzotriazole (HOBT) (146.9 mg, 0.97 mmol), and 1-(3-dimethylaminopropyl)-3-ethylcarbodiimide hydrochloride (EDC) (145.8 mg, 0.75 mmol) in 4 mL of anhydrous dimethylformamide (DMF) cooled to 0° C. and stirred under nitrogen for 0.5 h. This solution is then treated with a desired sulfonamide isostere and stirred at room temperature for 16 h. The solution is poured into 30 mL of 60% saturated aqueous sodium bicarbonate solution. The aqueous solution is then decanted from the organic residue. The organic residue is taken up in dichloromethane and washed with 10% aqueous citric acid, brine, dried over anhydrous magnesium sulfate, filtered and concentrated. Flash chromatography of the mixture on silica gel eluting with 1:1 hexane:ethyl acetate can be utilized and will afford the separated diastereomers.

EXAMPLE 14C
PART A

A solution of methyl 2-(bromomethyl)-acrylate (26.4 g, 0.148 mol) in 100 mL of methanol was treated with sodium methanesulfinate (15.1 g, 0.148 mol) portion wise over 10 m at room temperature. The solution was then stirred at room temperature for a period of 1.25 h and the solution concentrated in vacuo. The residue was then taken up in water and extracted four times with ethyl acetate. The combined ethyl acetate solution was washed with saturated sodium chloride, dried over anhydrous magnesium sulfate, filtered and concentrated to give a white solid, 20.7 g which was taken up in boiling acetone/methyl tert-butyl ether and allowed to stand whereupon crystals of pure methyl 2-(methylsulfonylmethyl) acrylate 18.0 g, 68% formed, mp 65–68 0° C.

PART B

A solution of methyl 2-(methylsulfonylmethyl) acrylate (970 mg, 5.44 mmol) in 15 mL of tetrahydrofuran was treated with a solution of lithium hydroxide (270 mg, 6.4 mmol) in 7 mL of water. The solution was stirred at room temperature for 5 m and then acidified to pH=1 with 1N aqueous potassium hydrogen sulfate and the solution extracted three times with ethyl acetate. The combined ethyl acetate solution was dried over anhydrous magnesium sulfate, filtered, and concentrated to give 793 mg, 89% of 2-(methylsulfonylmethyl) acrylic acid, mp 147–149 0° C.

PART C

A solution of 2-(methylsulfonylmethyl) acrylic acid (700 mg, 4.26 mmol) in 20 mL of methanol was charged into a Fisher-Porter bottle along with 10% palladium on carbon catalyst under a nitrogen atmosphere. The reaction vessel was sealed and flushed five times with nitrogen and then five times with hydrogen. The pressure was maintained at 50 psig for 16 h and then the hydrogen was replaced with nitrogen and the solution filtered through a pad of celite to remove the catalyst and the filterate concentrated in vacuo to give 682 mg 96% of 2-(R,S)-methyl-3-methylsulfonyl propionic acid.

PART D

A solution of 2-(R,S)-methyl-3(methylsulfonyl) propionic acid (263.5 mg, 1.585 mmol), N-hydroxybenzotriazole (HOBT) (322.2 mg, 2.13 mmol), and 1-(3-dimethylaminopropyl)-3-ethylcarbodiimide hydrochloride (EDC) (339.1 mg, 1.74 mmol) in 4 mL of anhydrous dimethylformamide (DMF) is cooled to 0° C. and stirred under nitrogen for 0.5 h. This solution is then treated with a desired sulfonamide and stirred at room temperature for 16 h. The solution is poured into 60 mL of 60% saturated aqueous sodium bicarbonate solution. The aqueous solution is then decanted from the organic residue. The organic residue is taken up in dichloromethane and washed with 10% aqueous citric acid, brine, dried over anhydrous magnesium sulfate, filtered and concentrated to give the desired product.

EXAMPLE 14D

Preparation of Sulfone Inhibitors From L-(+)-S-acetyl-β-mercaptoisobutyric Acid

PART A

A round-bottomed flask is charged with the desired sulfonamide isostere (2.575 mmol), for example, the amine from Example 3, Part C, can be coupled to L-(+)-S-acetyl-β-mercapto butyric acid in the presence of 1-(3-dimethylaminopropyl)-3-ethylcarbodiimide hydrochloride (EDC) (339.1 mg, 1.74 mmol), in 10 mL of $CH_2Cl_2$ and is allowed to stir at room temperature for 16 h. The solution is concentrated in vacuo and the residue taken up in ethyl acetate, washed with 1N $KHSO_4$ sat. aq. $NaHCO_3$, brine, dried over anhydrous $MgSO_4$, filtered and concentrated to give an oil which can be purified by radial chromatography on $SiO_2$ eluting with ethyl acetate to give the pure product.

PART B

A solution of the product of Part A (0.85 mmol) in 10 mL of methanol is treated with anhydrous ammonia for ca. 1 m at 0° C. The solution is stirred at that temperature for 16 h and then concentrated in vacuo to give the desired product that can be used directly in the next step without further purification.

PART C

A solution of the product of Part B (0.841 mmol) in 10 mL of dry toluene under nitrogen is treated in rapid succession with 1,8-diazabicyclo[5.4.0]undec-7-ene, (DBU), (128.1 mg, 0.841 mmol) and iodomethane (119.0 mg, 0.841 mmol). After 0.5 h at room temperature the reaction is diluted with ethyl acetate washed with 1N $KHSO_4$, sat. aq. $NaHCO_3$, brine. After the solution is dried over anhydrous $MgSO_4$, filtered and concentrated in vacuo the desired product is obtained and can be used directly in the next step.

PART D

A solution of the product of Part C (0.73 mmol) and sodium perborate (500 mg, 3.25 mmol) in 30 mL of glacial acetic acid is warmed to 55° C. for 16 h. The solution is concentrated in vacuo and then the residue is taken up in ethyl acetate, washed with water, sat. aq. $NaHCO_3$, brine, dried over anhydrous $MgSO_4$, filtered and concentrated to give the desired product.

Representative sulfones prepared according to the above general procedures are shown in Table 3.

TABLE 3

| Entry | R |
|---|---|
| 1 | $CH_3$— |
| 2 | $PhCH_2CH_2$— |
| 3 | Ph— |

General Procedure for Coupling Sulfonyl Compounds to Sulfonamides

A mixture of the sulfonyl alkanoyl compound (approximately 1 mmol), N-hydroxybenzotriazole (1.5 mmol), and 1-(3-dimethylaminopropyl)-3-ethylcarbodiimide hydrochloride (EDC) (1.2 mmol) is dissolved in a suitable solvent such as DMF and allowed to react for about 30 min. at 0° C. The sulfonamide (1.05 mmol) is dissolved in DMF, added to the above mixture and stirred at room temperature for a period of time sufficient for the reaction to take place. The solution is then poured into saturated aqueous $NaHCO_3$ and extracted with, for example, ethyl acetate. The extracts are washed, dried, filtered and concentrated. The resulting material is then crystallized from a suitable solvent or solvent mixture such as hexanes and ethyl acetate to produce the product.

Representative compounds prepared according to these general procedures are shown in the following Table.

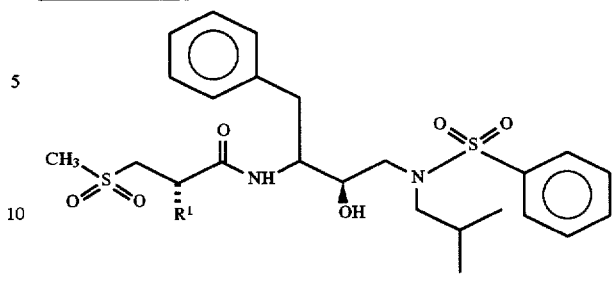

| Entry | $R^1$ |
|---|---|
| 1 | —$CH_3$ |
| 2 | —$CH_2CH_3$ |
| 3 | —$CH(CH_3)_2$ |
| 4 | —$C(CH_3)_3$ |

EXAMPLE 15

Utilizing the general and specific procedures shown in Examples 1–14, the compounds shown in Tables 4–8 could be prepared.

TABLE 4

| Entry | $R^3$ | $R^4$ |
|---|---|---|
| 1 | $CH_3$ | n-Butyl |
| 2 | i-Butyl | $CH_3$ |
| 3 | i-Butyl | n-Butyl |
| 4 | i-Butyl | sec-butyl |
| 5 | i-Propyl | n-Butyl |
| 6 | i-Propyl | n-Butyl |
| 7 | $C_6H_5$ | n-Butyl |
| 8 | —$CH_2$-cyclohexyl | n-Butyl |
| 9 | —$CH_2$-phenyl | $CF_3$ |
| 10 | —$CH_2$-phenyl | Phenyl |
| 11 | -cyclohexyl | $CH_3$ |
| 12 | i-Butyl | n-Propyl |
| 13 | i-Butyl | —$CH_2CH(CH_3)_2$ |
| 14 | R)—$CH(CH_3)$-phenyl | $CH_3$ |

TABLE 4-continued

[Structure: CH₃-S(O₂)-CH₂-CH(CH₃)-C(O)-NH-CH(CH₂Ph)-CH(OH)-CH₂-N(R³)-S(O₂)-R⁴]

| Entry | R³ | R⁴ |
|---|---|---|
| 15 | -CH₂-cyclohexyl | i-Propyl |
| 16 | -CH₂-cyclohexyl | -CH₂CH₂CH(CH₃)₂ |
| 17 | i-Butyl | -CH₂CH₃ |
| 18 | i-Butyl | -CH(CH₃)₂ |
| 19 | i-Butyl | cyclohexyl |
| 20 | i-Butyl | cyclohexyl |
| 21 | -CH₂-cyclohexyl | -(CH₂)₂CH(CH₃)₂ |
| 22 | (CH₂)₂CH(CH₃)₂ | -CH(CH₃)₂ |
| 23 | i-Butyl | -CH(CH₃)₂ |
| 24 | i-Butyl | -C(CH₃)₃ |
| 25 | n-Butyl | -C(CH₃)₃ |
| 26 | -CH₂-naphthyl | -CH₃ |
| 27 | -CH₂-naphthyl | -C₆H₅ |
| 28 | -(CH₂)₂CH(CH₃)₂ | -C(CH₃)₃ |
| 29 | -(CH₂)₂CH(CH₃)₂ | sec-butyl |
| 30 | -CH₂C₆H₅ | Ethyl |
| 31 | -CH₂C₆H₅ | Phenyl |
| 32 | -(CH₂)₂C₆H₅ | -CH₃ |
| 33 | -(CH₂)₂C₆H₅ | Phenyl |
| 34 | n-Butyl | Ethyl |
| 35 | n-Pentyl | Ethyl |
| 36 | n-Hexyl | Ethyl |
| 37 | -CH₂-phenyl | Ethyl |
| 38 | -CH₂C(CH₃)₃ | -CH₃ |
| 39 | -CH₂C(CH₃)₃ | thienyl |
| 40 | -CH₂CH₂-morpholinyl | -CH₃ |
| 41 | -CH₂C₆H₅OCH₃(para) | -CH₃ |
| 42 | -CH₂-(3-pyridyl) | -CH₃ |
| 43 | -CH₂-(4-pyridyl) | -CH₃ |
| 44 | -(CH₂)₂C(CH₃)₃ | Ethyl |
| 45 | -(CH₂)₂C(CH₃)₃ | n-Propyl |
| 46 | -(CH₂)₄OH | -CH₃ |
| 47 | -(CH₂)₄OH | Phenyl |
| 48 | -CH₂-(4-F-phenyl) | -CH₃ |
| 49 | -CH₂-(4-pyridyl) | Phenyl |
| 50 | -CH₂CH(CH₃)₂ | Ethyl |

TABLE 5

[Structure: CH₃-S(O₂)-CH₂-CH(R¹)-C(O)-NH-CH(CH₂Ph)-CH(OH)-CH₂-N(iBu)-S(O₂)-C₆H₅]

| Entry | R¹ |
|---|---|
| 1 | CH₂SO₂CH₃ |
| 2 | (R) -CH(OH)CH₃ |
| 3 | (R,S)CH₂SOCH₃ |
| 4 | CH₂SO₂NH₂ |
| 5 | CH₂SCH₃ |
| 6 | CH₂CH(CH₃)₂ |
| 7 | CH₂CH₂C(O)NH₂ |
| 8 | (S)-CH(OH)CH₃ |
| 9 | -CH₂C≡-CH |

TABLE 6

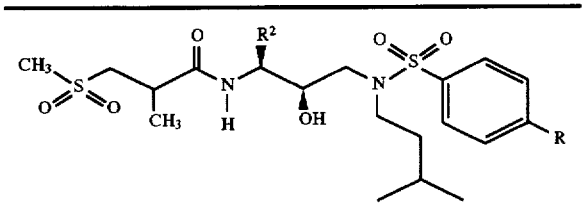

| Entry | R | R² |
|---|---|---|
| 1 | —OCH₃ | n-Bu |
| 2 | —OCH₃ | cyclohexylmethyl |
| 3 | —NHA_C | n-Bu |
| 4 | —NH₂ | n-Bu |
| 5 | —OCH₃ | C₆H₅CH₂ |
| 6 | —NHA_C | C₆H₅CH₂ |
| 7 | —NH₂ | C₆H₅CH₂ |
| 8 | —NHA_C | cyclohexylmethyl |
| 9 | —C(CH₃)₃ | n-Bu |
| 10 | —NH₂ | cyclohexylmethyl |
| 11 | —C(CH₃)₃ | C₆H₅CH₂ |
| 12 | —OCH₃ | 2-naphthylmethyl |
| 13 | —NHA_C | 2-naphthylmethyl |
| 14 | —NH₂ | 2-naphthylmethyl |
| 15 | —C(CH₃)₃ | 2-naphthylmethyl |
| 16 | —OCH₃ | p-F(C₆H₄)CH₂ |
| 17 | —NH₂ | p-F(C₆H₄)CH₂ |
| 18 | —NHA_C | p-F(C₆H₄)CH₂ |
| 19 | —C(CH₃)₃ | p-F(C₆H₄)CH₂ |
| 20 | —CF₃ | C₆H₅CH₂ |
| 21 | —CO₂CH₃ | C₆H₅CH₂ |
| 22 | —F | C₆H₅CH₂ |
| 23 | Cl | C₆H₅CH₂ |

TABLE 7

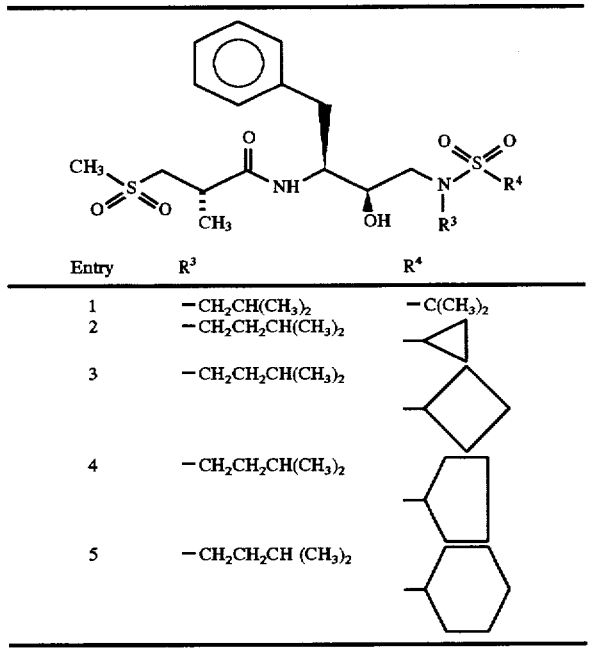

| Entry | R³ | R⁴ |
|---|---|---|
| 1 | —CH₂CH(CH₃)₂ | —C(CH₃)₂ |
| 2 | —CH₂CH₂CH(CH₃)₂ | (cyclopropyl) |
| 3 | —CH₂CH₂CH(CH₃)₂ | (cyclobutyl) |
| 4 | —CH₂CH₂CH(CH₃)₂ | (cyclopentyl) |
| 5 | —CH₂CH₂CH (CH₃)₂ | (cyclohexyl) |

TABLE 8

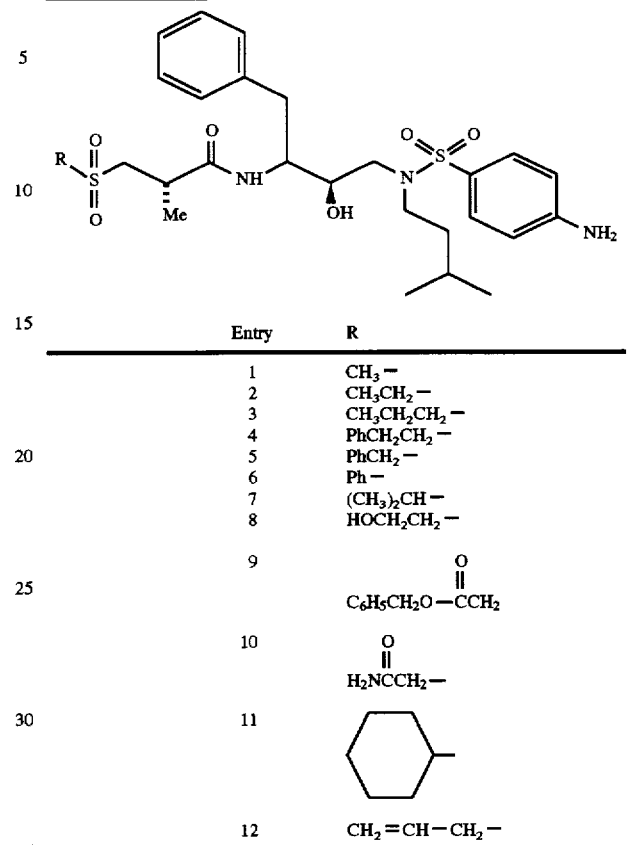

| Entry | R |
|---|---|
| 1 | CH₃— |
| 2 | CH₃CH₂— |
| 3 | CH₃CH₂CH₂— |
| 4 | PhCH₂CH₂— |
| 5 | PhCH₂— |
| 6 | Ph— |
| 7 | (CH₃)₂CH— |
| 8 | HOCH₂CH₂— |
| 9 | C₆H₅CH₂O—C(=O)CH₂ |
| 10 | H₂NC(=O)CH₂— |
| 11 | (cyclohexyl)— |
| 12 | CH₂=CH—CH₂— |

EXAMPLE 16

The compounds of the present invention are effective HIV protease inhibitors. Utilizing an enzyme assay as described below, the compounds set forth in the examples herein disclosed inhibited the HIV enzyme. The preferred compounds of the present invention and their calculated $IC_{50}$ (inhibiting concentration 50%, i.e., the concentration at which the inhibitor compound reduces enzyme activity by 50%) values are shown in Table 16. The enzyme method is described below. The substrate is 2-aminobenzoyl-Ile-Nle-Phe(p-NO₂)-Gln-ArgNH₂. The positive control is MVT-101 (Miller, M. et al Science, 246, 1149 (1989)] The assay conditions are as follows:

Assay buffer:

20 mM sodium phosphate, pH 6.4

20% glycerol 1 mM EDTA 1 mM DTT 0.1% CHAPS

The above described substrate is dissolved in DMSO, then diluted 10 fold in assay buffer. Final substrate concentration in the assay is 80 μM.

HIV protease is diluted in the assay buffer to a final enzyme concentration of 12.3 nanomolar, based on a molecular weight of 10,780.

The final concentration of DMSO is 14% and the final concentration of glycerol is 18%. The test compound is dissolved in DMSO and diluted in DMSO to 10× the test concentration; 10 μl of the enzyme preparation is added, the materials mixed and then the mixture is incubated at ambient temperature for 15 minutes. The enzyme reaction is initiated by the addition of 40 μl of substrate. The increase in fluorescence is monitored at 4 time points (0, 8, 16 and 24 minutes) at ambient temperature. Each assay is carried out in duplicate wells.

TABLE 9

| Example No. | IC$_{50}$ (nanomolar) |
|---|---|
| 2 | 3.2 |
| 3 | 3.2 |
| 4 | 3 |
| 5 | 13 |
| 6 | 8.8 |
| 7 | 1.9 |
| 8 | 3.1 |
| 9 | 4.1 |
| 10 | 2.2 |
| 11 | 7.8 |
| 12 | 38 |

EXAMPLE 17

The effectiveness of compounds of the present invention were determined in a CEM cell assay.

The HIV inhibition assay method of acutely infected cells is an automated tetrazolium based calorimetric assay essentially that reported by Pauwles et al. *J. Virol. Methods*, 20, 309–321 (1988). Assays were performed in 96-well tissue culture plates. CEM cells, a CD4$^+$ cell line, were grown in RPMI-1640 medium (Gibco) supplemented with a 10% fetal calf serum and were then treated with polybrene (2 μg/ml). An 80 μl volume of medium containing 1×10$^4$ cells was dispensed into each well of the tissue culture plate. To each well was added a 100 μl volume of test compound dissolved in tissue culture medium (or medium without test compound as a control) to achieve the desired final concentration and the cells were incubated at 37° C. for 1 hour. A frozen culture of HIV-1 was diluted in culture medium to a concentration of 5×10$^4$ TCID$_{50}$ per ml (TCID$_{50}$=the dose of virus that infects 50% of cells in tissue culture), and a 20 μL volume of the virus sample (containing 1000 TCID$_{50}$ of virus) was added to wells containing test compound and to wells containing only medium (infected control cells). Several wells received culture medium without virus (uninfected control cells). Likewise, the intrinsic toxicity of the test compound was determined by adding medium without virus to several wells containing test compound. In summary, the tissue culture plates contained the following experiments:

| | Cells | Drug | Virus |
|---|---|---|---|
| 1. | + | − | − |
| 2. | + | + | − |
| 3. | + | − | + |
| 4. | + | + | + |

In experiments 2 and 4 the final concentrations of test compounds were 1, 10, 100 and 500 μg/ml. Either azidothymidine (AZT) or dideoxyinosine (ddI) was included as a positive drug control. Test compounds were dissolved in DMSO and diluted into tissue culture medium so that the final DMSO concentration did not exceed 1.5% in any case. DMSO was added to all control wells at an appropriate concentration.

Following the addition of virus, cells were incubated at 37° C. in a humidified, 5% CO$_2$ atmosphere for 7 days. Test compounds could be added on days 0, 2 and 5 if desired. On day 7, post-infection, the cells in each well were resuspended and a 100 μl sample of each cell suspension was removed for assay. A 20 μL volume of a 5 mg/ml solution of 3-(4,5-dimethylthiazol-2-yl)-2,5-diphenyltetrazolium bromide (MTT) was added to each 100 μL cell suspension, and the cells were incubated for 4 hours at 27° C. in a 5% CO$_2$ environment. During this incubation, MTT is metabolically reduced by living cells resulting in the production in the cell of a colored formazan product. To each sample was added 100 μl of 10% sodium dodecylsulfate in 0.01N HCl to lyse the cells, and samples were incubated overnight. The absorbance at 590 nm was determined for each sample using a Molecular Devices microplate reader. Absorbance values for each set of wells is compared to assess viral control infection, uninfected control cell response as well as test compound by cytotoxicity and antiviral efficacy.

TABLE 10

| Example No. | IC$_{50}$ (nM) | EC$_{50}$ (nM) | TD$_{50}$ (nM) |
|---|---|---|---|
| 2 | 3.2 | 12 | 90,000 |
| 3 | 3.2 | 10 | 213,000 |
| 4 | 3 | 12 | >1,000,000 |
| 5 | 13 | 25 | 438,000 |
| 6 | 8.8 | 29 | 133,000 |
| 7 | 1.9 | 2 | >1,000,000 |
| 8 | 3.1 | 9 | >1,000,000 |
| 9 | 4.1 | 16 | >1,000,000 |
| 10 | 22 | 223 | 860,000 |
| 11 | 7.8 | 45 | 170,000 |
| 12 | 38 | 87 | 77,000 |

Utilizing the procedures set forth above in the examples along with the general description, it is contemplated that the compounds listed below could be prepared and that such compounds would have activities as HIV protease inhibitors substantially similar to the activities of the compounds set forth in the examples.

The compounds of the present invention are effective antiviral compounds and, in particular, are effective retroviral inhibitors as shown above. Thus, the subject compounds are effective HIV protease inhibitors. It is contemplated that the subject compounds will also inhibit other retroviruses such as other lentiviruses in particular other strains of HIV, e.g. HIV-2, human T-cell leukemia virus, respiratory syncitial virus, simian immunodeficiency virus, feline leukemia virus, feline immuno-deficiency virus, hepadnavirus, cytomegalovirus and picornavirus. Thus, the subject compounds are effective in the treatment and/or proplylaxis of retroviral infections.

Compounds of the present can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Total daily dose administered to a host in single or divided doses may be in amounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming-agents.

While the compounds of the invention can be administered as the sole active pharmaceutical agent, they can also be used in combination with one or more immunomodulators, antiviral agents or other antiinfective agents. For example, the compounds of the invention can be administered in combination with AZT, DDI, DDC or with N-butyl-1-deoxynojirimycin for the prophylaxis and/or treatment of AIDS. When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound represented by the formula:

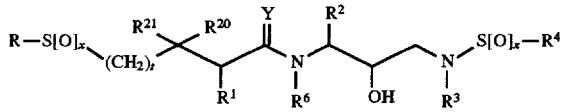

or a pharmaceutically acceptable salt, prodrug or ester thereof wherein:

R represents hydrogen, alkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminocarbonylalkyl, aminoalkylcarbonylalkyl, aminoalkyl, alkylcarbonylalkyl, aryloxyalkylcarbonylalkyl, aralkoxycarbonylalkyl radicals and mono- and disubstituted aminocarbonylalkyl, aminoalkylcarbonylalkyl and aminoalkyl radicals wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted radical, said substituents along with the nitrogen atom to which they are attached, form a heterocycloalkyl or a heteroaryl radical;

each x independently represents 0, 1 or 2;

t represents either 0 or 1;

$R^1$, $R^{20}$ and $R^{21}$ independently represent hydrogen, $-CH_2SO_2NH_2$, $-CH_2CO_2CH_3$, $-CO_2CH_3$, $-CONH_2$, $-CH_2C(O)NHCH_3$, $-C(CH_3)_2(SH)$, $-C(CH_3)_2(SCH_3)$, $-C(CH_3)_2(S[O]CH_3)$, $-C(CH_3)_2(S[O]_2CH_3)$, alkyl, haloalkyl, alkenyl, alkynyl and cycloalkyl radicals, and amino acid side chains selected from asparagine, S-methyl cysteine and the sulfoxide (SO) and sulfone ($SO_2$) derivatives thereof, isoleucine, allo-isoleucine, alanine, leucine, tert-leucine, phenylalanine, ornithine, histidine, norleucine, glutamine, threonine, glycine, allo-threonine, serine, O-alkyl serine, aspartic acid, beta-cyano alanine and valine side chains;

$R^2$ represents alkyl, aryl, cycloalkyl, cycloalkylalkyl and aralkyl radicals, which radicals are optionally substituted with a group selected from $-NO_2$, $-C\equiv N, CF_3$ $-OR^9$, $-SR^9$, and halogen and alkylradicals, wherein $R^9$ represents hydrogen and alkyl radicals;

$R^3$ represents hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

Y represents O, S and $NR^{15}$ wherein $R^{15}$ represents hydrogen and radicals as defined for $R^3$;

$R^4$ represents radicals as defined by $R^3$ except for hydrogen; and $R^6$ represents hydrogen and alkyl radicals.

2. Compound represented by the formula:

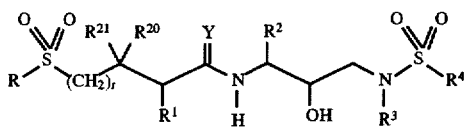

or a pharmaceutically acceptable salt, prodrug or ester thereof, wherein;

R represents alkyl, alkenyl, alkynyl, cycloalkyl, cycloalkylalkyl, heterocycloalkyl, heterocycloalkylalkyl, aryl, heteroaryl, aralkyl, heteroalkyl, aminocarbonylalkyl, aminoalkylcarbonylalkyl, hydroxyalkyl, heteroaralkyl, alkylcarbonylalkyl, aryloxyalkylcarbonylalkyl and aralkoxycarbonylalkyl radicals;

$R^1$, $R^{20}$ and $R^{21}$ independently represent hydrogen, $-CH_2SO_2NH_2$, $-CH_2CO_2CH_3$, $-CO_2CH_3$, $-CONH_2$, $-CH_2C(O)NHCH_3$, $-C(CH_3)_2(SCH_3)$, $-C(CH_3)_2(S[O]CH_3)$, $-C(CH_3)_2(S[O]_2CH_3)$, alkyl, haloalkyl, alkenyl, alkynyl and cycloalkyl radicals, and amino acid side chains selected from asparagine, S-methyl cysteine and the sulfoxide (SO) and sulfone ($SO_2$) derivatives thereof, isoleucine, allo-isoleucine, alanine, leucine, tert-leucine, phenylalanine, ornithine, histidine, norleucine, glutamine, threonine, glycine, allo-threonine, serine, O-alkyl serine, aspartic acid, beta-cyano alanine and valine side chains;

$R^2$ represents alkyl, aryl, cycloalkyl, cycloalkylalkyl, and aralkyl radicals, which radicals are optionally substituted with a group selected from halogen and alkyl radicals, $NO_2$, $-C\equiv N, CF_3$, $-OR^9$ and $-SR^9$ wherein $R^9$ represents hydrogen and alkyl radicals, and halogen radicals;

$R^3$ represents hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

$R^4$ represents radicals as defined by $R^3$ except for hydrogen;

t represents 0 or 1; and

Y represents O, S, and $NR^{15}$ wherein $R^{15}$ represents hydrogen and radicals as defined for $R^3$.

3. Compound of claim 2 wherein R represents alkyl, aryl and aralkyl radicals.

4. Compound of claim 2 wherein R represents methyl and phenethyl radicals.

5. Compound of claim 2 wherein R represents methyl.

6. Compound of claim 2 wherein R represents phenethyl.

7. Compound of claim 2 wherein $R^1$ represents hydrogen, alkyl, alkenyl and alkynyl radicals.

8. Compound of claim 2 wherein $R^1$ represents methyl, ethyl, propargyl, t-butyl, isopropyl and sec-butyl radicals.

9. Compound of claim 2 wherein $R^1$ represents methyl, ethyl and t-butyl radicals.

10. Compound of claim 2 wherein $R^1$ represents a methyl radical when t is 0.

11. Compound of claim 2 wherein $R^1$ represents an ethyl radical when t is 0.

12. Compound of claim 2 wherein $R^1$ represents alkyl radicals having from 1 to about 4 carbon atoms.

13. Compound of claim 2 wherein R and $R^1$ both represent a methyl radical.

14. Compound of claim 2 wherein R represents a methyl radical and $R^1$ represents an ethyl radical.

15. Compound of claim 2 wherein R represents a methyl radical, $R^1$ represents a methyl radical and t is 0.

16. Compound of claim 2 wherein t is 0.

17. Compound of claim 2 wherein t is 1.

18. Compound of claim 2 wherein $R^2$ represents alkyl, cycloalkylalkyl and aralkyl radicals, which radicals are optionally substituted with halogen radicals and radicals represented by the formula —$OR^9$ and —$SR^9$ herein $R^9$ represents alkyl radicals.

19. Compound of claim 2 wherein $R^2$ represents alkyl, cycloalkylalkyl and aralkyl radicals.

20. Compound of claim 2 wherein $R^2$ represents aralkyl radicals.

21. Compound of claim 2 wherein $R^2$ represents $CH_3SCH_2CH_2$—, iso-butyl, n-butyl, benzyl, 4-fluorobenzyl, 2-naphthylmethyl and cyclohexylmethyl radicals.

22. Compound of claim 2 wherein $R^2$ represents an n-butyl and iso-butyl radicals.

23. Compound of claim 2 wherein $R^2$ represents benzyl, 4-fluorobenzyl and 2-naphthylmethyl radicals.

24. Compound of claim 2 wherein $R^2$ represents a cyclohexylmethyl radical.

25. Compound of claim 2 wherein $R^3$ and $R^4$ independently represent alkyl, alkenyl, hydroxyalkyl, alkoxyalkyl, haloalkyl, cycloalkyl, cycloalkylalkyl, heterocycloalkyl, heteroaryl, heterocycloalkylalkyl, aryl, aralkyl and heteroaralkyl radicals.

26. Compound of claim 25 wherein $R^3$ represents an alkyl radical and $R^4$ represents an aryl radical.

27. Compound of claim 25 wherein $R^3$ and $R^4$ independently represent alkyl and aryl radicals.

28. Compound of claim 25 wherein $R^3$ and $R^4$ independently represent alkyl, cycloalkyl, cycloalkylalkyl, aralkyl and aryl radicals.

29. Compound of claim 25 wherein $R^3$ and $R^4$ independently represent alkyl, cycloalkyl and cycloalkylalkyl radicals.

30. Compound of claim 25 wherein $R^3$ and $R^4$ independently represent alkyl, heterocycloalkyl and heterocycloalkylalkyl radicals.

31. Compound of claim 25 wherein $R^3$ and $R^4$ independently represent alkyl, aryl and aralkyl radicals.

32. Compound of claim 25 wherein $R^4$ represents phenyl, p-fluorophenyl, p-nitrophenyl, p-methoxyphenyl, p-chlorophenyl and p-aminophenyl radicals.

33. Compound of claim 2 wherein $R^3$ represents alkyl radicals having from about 2 to about 5 carbon atoms.

34. Compound of claim 2 wherein $R^3$ represents n-pentyl, n-hexyl, n-propyl, i-butyl, neo-pentyl, i-amyl, and n-butyl radicals.

35. Compound of claim 2 wherein $R^3$ represents alkyl radicals having from about 2 to about 5 carbon atoms, and cycloalkyl and cycloalkylalkyl radicals having from about 6 to about 10 carbon atoms; and $R^4$ represents aryl and heteroaryl radicals which may be substituted with substituents selected from chloro, fluoro, nitro, methoxy and amino substituents.

36. Compound of claim 2 wherein $R^3$ represents benzyl, para-fluorobenzyl, para-methoxybenzyl, para-methylbenzyl, and 2-naphthylmethyl radicals and $R^4$ represents phenyl radicals and substituted phenyl radicals, wherein substituents of the substituted phenyl radical are selected from chloro, fluoro, nitro, methoxy and amino substituents.

37. Compound of claim 2 wherein $R^3$ is cyclohexylmethyl and $R^4$ is phenyl.

38. Compound of claim 2 wherein $R^3$ is i-amyl and $R^4$ is phenyl.

39. Compound of claim 2 wherein $R^3$ is i-butyl and $R^4$ is phenyl.

40. Compound of claim 2 wherein $R^3$ is n-butyl and $R^4$ is phenyl.

41. Compound of claim 2 wherein $R^3$ is neo-pentyl and $R^4$ is phenyl.

42. Compound of claim 2 wherein $R^4$ represents aryl radicals.

43. Compound of claim 2 wherein $R^4$ represents substituted aryl and heteroaryl radicals wherein substituents are selected form halo, nitro, alkoxy, and amino radicals.

44. Compound of claim 2 wherein $R^3$ and $R^4$ independently represent alkyl, cycloalkyl, cycloalkylalkyl, aryl and aralkyl radicals.

45. Compound of claim 2 wherein $R^3$ represents heteroaralkyl radicals and $R^4$ is an aryl radical.

46. Compound of claim 2 wherein $R^3$ is a p-fluorobenzyl radical and $R^4$ is an aryl radical.

47. Compound of claim 2 wherein $R^3$ is a 4-pyridylmethyl radical or its N-oxide and $R^4$ is an aryl radical.

48. Compound of claim 2 wherein $R^4$ represents methyl and cyclohexyl radicals and $R^3$ represents an alkyl radical.

49. Compound of claim 2 wherein $R^3$ and $R^4$ independently represent aryl radicals optionally substituted with substituents selected from amino, alkoxy, halo, and nitro substituents.

50. Compound of claim 2 wherein $R^{20}$ and $R^{21}$ are both hydrogen and $R^1$ represents an alkyl radical having from 1 to about 4 carbon atoms.

51. Compound of claim 2 wherein $R^{20}$ and $R^{21}$ are both hydrogen and $R^1$ represents, —$CH_2SO_2NH_2$, $CO_2NH_2$, $CO_2CH_3$, alkyl and cycloalkyl radicals and amino acid side chains selected from asparagine, S-methyl cysteine and the sulfone and sulfoxide derivatives thereof, histidine, norleucine, glutamine, glycine, allo-isoleucine, alanine, threonine, isoleucine, leucine, tert-leucine, phenylalanine, ornithine, allo-threonine, serine, O-methyl serine, aspartic acid, beta-cyano alanine and valine side chains.

52. Compound of claim 2 wherein t is 0, $R^1$ represents an alkyl radical and R represents an alkyl, cycloalkyl, cycloalkylalkyl or an aryl radical.

53. Compound of claim 2 wherein R represents a heteroaryl radical.

54. Compound of claim 2 wherein R represents an alkyl or aryl radical.

55. Compound of claim 2 wherein t is O, $R^1$ represents a methyl or ethyl radical and R represents a methyl or phenethyl radical.

56. Compound of claim 2 wherein R represents an aralkylcarbonylalkyl, aryloxycarbonylalkyl, alkanoylalkyl, aminocarbonylalkyl, or a mono- or dialkylaminocarbonylalkyl radical.

57. Compound of claim 2 wherein R represents an aryloxycarbonylalkyl or alkanoylalkyl radical.

58. Compound of claim 2 wherein R represents an aminocarbonylalkyl radical, a monosubstituted aminoalkanoylalkyl radical or disubstituted aminoalkanoylalkyl radical.

59. Compound of claim 2 where R represents an aralkylcarbonylalkyl radical.

60. Compound of claim 2 where t is 1 and $R^1$ is a methyl radical.

61. Compound of claim 60 where R represents an alkyl, cycloalkyl, cycloalkylalkyl, aryl or aralkyl radical.

62. Compound of claim 60 where R represents a methyl, cyclohexyl, cyclohexylmethyl, phenyl, benzyl or phenethyl radical.

63. Compound of claim 2 wherein t is 1, $R^{20}$ and $R^{21}$ are both hydrogen and $R^1$ is methyl or ethyl.

64. Compound of claim 60 wherein R represents an aminocarbonylalkyl or a mono- or dialkylaminocarbonylalkyl radical.

65. Compound of claim 60 where R represents an N,N-dimethylaminocarbonylalkyl radical.

66. A pharmaceutical composition comprising a compound of claim 1 and a pharmaceutically acceptable carrier.

67. A pharmaceutical composition comprising a compound of claim 2 and a pharmaceutically acceptable carrier.

68. Method of inhibiting a retroviral protease comprising administering a protease inhibiting amount of a composition of claim 66.

69. Method of claim 68 wherein the retroviral protease is HIV protease.

70. Method of treating a retroviral infection comprising administering an effective amount of a composition of claim 66.

71. Method of claim 70 wherein the retroviral infection is an HIV infection.

72. Method for treating AIDS comprising administering an effective amount of a composition of claim 66.

73. Method of inhibiting a retroviral protease comprising administering a protease inhibiting amount of a composition of claim 67.

74. Method of claim 73 wherein the retroviral protease is HIV protease.

75. Method of treating a retroviral infection comprising administering an effective amount of a composition of claim 67.

76. Method of claim 75 wherein the retroviral infection is an HIV infection.

77. Method for treating AIDS comprising administering an effective amount of a composition of claim 67.

* * * * *